(12) United States Patent
Michihata

(10) Patent No.: US 10,149,600 B2
(45) Date of Patent: *Dec. 11, 2018

(54) MEDICAL SIGNAL PROCESSING DEVICE AND MEDICAL OBSERVATION SYSTEM

(71) Applicant: Sony Olympus Medical Solutions Inc., Tokyo (JP)

(72) Inventor: Taihei Michihata, Kanagawa (JP)

(73) Assignee: Sony Olympus Medical Solutions Inc., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/384,816

(22) Filed: Dec. 20, 2016

(65) Prior Publication Data

US 2017/0202435 A1    Jul. 20, 2017

(30) Foreign Application Priority Data

Jan. 15, 2016 (JP) .................. 2016-006643

(51) Int. Cl.
  *G06K 9/00* (2006.01)
  *A61B 1/00* (2006.01)
  (Continued)

(52) U.S. Cl.
  CPC ...... *A61B 1/00018* (2013.01); *A61B 1/00009* (2013.01); *A61B 1/00186* (2013.01); *A61B 1/04* (2013.01); *G06T 1/20* (2013.01); *H04N 7/183* (2013.01); *H04N 9/07* (2013.01); *H04N 5/2256* (2013.01); *H04N 2005/2255* (2013.01)

(58) Field of Classification Search
  None
  See application file for complete search history.

(56) References Cited

U.S. PATENT DOCUMENTS 5,649,897 A *  7/1997  Nakamura ......... A61B 1/00193
                                                    348/45
5,878,159 A *  3/1999  Taleblou .................. G06T 1/00
                                                    348/65

(Continued)

FOREIGN PATENT DOCUMENTS

JP    2006-26134    2/2006
JP    2009-61032    3/2009

*Primary Examiner* — Shervin Nakhjavan
(74) *Attorney, Agent, or Firm* — Oblon, McClelland, Maier & Neustadt, L.L.P.

(57) ABSTRACT

A medical signal processing device receives an image signal in accordance with a result of examining inside of a subject and processes the image signal that includes a plurality of pixel data groups of respective pixels arrayed at a constant interval among pixels sequentially arrayed in a predetermined direction in an image made of pixels arrayed in a matrix. The pixel data groups are data of respective pixels that are different from each other, and the pixel data groups are input in the medical signal processing device in parallel. The medical signal processing device includes a distribution processing unit configured to generate a plurality of distributed image signals by combining, among the pixel data groups, pixel data groups of respective pixels that are separate from each other, and the distributed image signals are transmitted to an external medical control device through a plurality of respective signal transmission paths.

8 Claims, 17 Drawing Sheets

(51) Int. Cl.
   *G06T 1/20*    (2006.01)
   *H04N 9/07*    (2006.01)
   *H04N 7/18*    (2006.01)
   *A61B 1/04*    (2006.01)
   *H04N 5/225*   (2006.01)

(56) References Cited

U.S. PATENT DOCUMENTS

| | | | | |
|---|---|---|---|---|
| 7,292,275 | B2* | 11/2007 | Masuyama | G02B 21/365 |
| | | | | 348/221.1 |
| 7,587,261 | B2* | 9/2009 | Hopkins | G06T 1/0007 |
| | | | | 382/153 |
| 8,449,453 | B2* | 5/2013 | Fujimoto | A61B 1/00006 |
| | | | | 348/525 |
| 2008/0123097 | A1* | 5/2008 | Muhammed | G01J 3/02 |
| | | | | 356/419 |
| 2011/0213203 | A1* | 9/2011 | Minai | A61B 1/00009 |
| | | | | 600/109 |
| 2012/0127292 | A1* | 5/2012 | Yamazaki | A61B 1/00009 |
| | | | | 348/68 |
| 2013/0012777 | A1* | 1/2013 | Baum | A61B 1/00013 |
| | | | | 600/110 |
| 2015/0022647 | A1* | 1/2015 | Takei | A61B 1/00186 |
| | | | | 348/70 |

* cited by examiner

FIG.3A

| 0<br>(CA) | 1<br>(CB) | 2<br>(CC) | 3<br>(CD) | 4<br>(CE) | 5<br>(CF) | 6<br>(CG) | 7<br>(CH) | 8<br>(CI) | 9<br>(CJ) | 10<br>(CA) | ...... |
|---|---|---|---|---|---|---|---|---|---|---|---|
| △△<br>(CA) | △□<br>(CB) | △○<br>(CC) | △×<br>(CD) | □□<br>(CE) | □△<br>(CF) | □○<br>(CG) | □×<br>(CH) | ○△<br>(CI) | ○□<br>(CJ) | ○×<br>(CA) | ...... |

| | | | | | | | | | | |
|---|---|---|---|---|---|---|---|---|---|---|
| (a) FIRST CHANNEL CA | 0(9) | 0(8) | 0(7) | 0(6) | 0(5) | 0(4) | 0(3) | 0(2) | 0(1) | 0(0) |
| (b) SECOND CHANNEL CB | 1(9) | 1(8) | 1(7) | 1(6) | 1(5) | 1(4) | 1(3) | 1(2) | 1(1) | 1(0) |
| (c) THIRD CHANNEL CC | 2(9) | 2(8) | 2(7) | 2(6) | 2(5) | 2(4) | 2(3) | 2(2) | 2(1) | 2(0) |
| (d) FOURTH CHANNEL CD | 3(9) | 3(8) | 3(7) | 3(6) | 3(5) | 3(4) | 3(3) | 3(2) | 3(1) | 3(0) |
| (e) FIFTH CHANNEL CE | 4(9) | 4(8) | 4(7) | 4(6) | 4(5) | 4(4) | 4(3) | 4(2) | 4(1) | 4(0) |
| (f) SIXTH CHANNEL CF | 5(9) | 5(8) | 5(7) | 5(6) | 5(5) | 5(4) | 5(3) | 5(2) | 5(1) | 5(0) |
| (g) SEVENTH CHANNEL CG | 6(9) | 6(8) | 6(7) | 6(6) | 6(5) | 6(4) | 6(3) | 6(2) | 6(1) | 6(0) |
| (h) EIGHTH CHANNEL CH | 7(9) | 7(8) | 7(7) | 7(6) | 7(5) | 7(4) | 7(3) | 7(2) | 7(1) | 7(0) |
| (i) NINTH CHANNEL CI | 8(9) | 8(8) | 8(7) | 8(6) | 8(5) | 8(4) | 8(3) | 8(2) | 8(1) | 8(0) |
| (j) TENTH CHANNEL CJ | 9(9) | 9(8) | 9(7) | 9(6) | 9(5) | 9(4) | 9(3) | 9(2) | 9(1) | 9(0) |

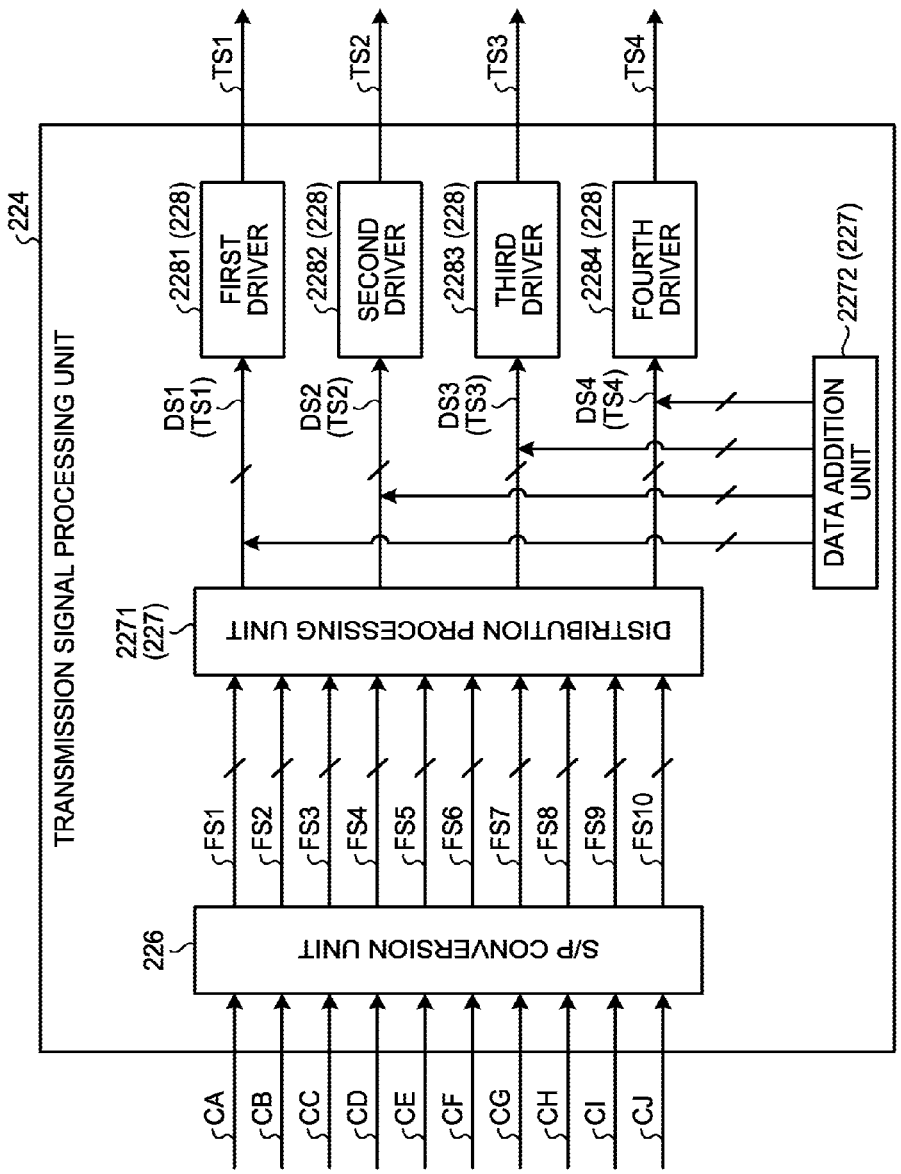

FIG.5

| | FS1 | FS2 | FS3 | FS4 | FS5 | FS6 | FS7 | FS8 | FS9 | FS10 |
|---|---|---|---|---|---|---|---|---|---|---|
| | EAV1 | EAV1 | EAV1 | EAV1 | EAV1 | EAV1 | EAV1 | EAV1 | EAV1 | EAV1 |
| | EAV2 | EAV2 | EAV2 | EAV2 | EAV2 | EAV2 | EAV2 | EAV2 | EAV2 | EAV2 |
| | EAV3 | EAV3 | EAV3 | EAV3 | EAV3 | EAV3 | EAV3 | EAV3 | EAV3 | EAV3 |
| | EAV4 | EAV4 | EAV4 | EAV4 | EAV4 | EAV4 | EAV4 | EAV4 | EAV4 | EAV4 |
| | 4249 | 4248 | 4247 | 4246 | 4245 | 4244 | 4243 | 4242 | 4241 | 4240 |
| | 4239 | 4238 | 4237 | 4236 | 4235 | 4234 | 4233 | 4232 | 4231 | 4230 |
| | 4229 | 4228 | 4227 | 4226 | 4225 | 4224 | 4223 | 4222 | 4221 | 4220 |
| | 4219 | 4218 | 4217 | 4216 | 4215 | 4214 | 4213 | 4212 | 4211 | 4210 |
| | 4209 | 4208 | 4207 | 4206 | 4205 | 4204 | 4203 | 4202 | 4201 | 4200 |
| | 4199 | 4198 | 4197 | 4196 | 4195 | 4194 | 4193 | 4192 | 4191 | 4190 |
| | ⋮ | ⋮ | ⋮ | ⋮ | ⋮ | ⋮ | ⋮ | ⋮ | ⋮ | ⋮ |
| | 169 | 168 | 167 | 166 | 165 | 164 | 163 | 162 | 161 | 160 |
| | 159 | 158 | 157 | 156 | 155 | 154 | 153 | 152 | 151 | 150 |
| | 149 | 148 | 147 | 146 | 145 | 144 | 143 | 142 | 141 | 140 |
| | 139 | 138 | 137 | 136 | 135 | 134 | 133 | 132 | 131 | 130 |
| | 129 | 128 | 127 | 126 | 125 | 124 | 123 | 122 | 121 | 120 |
| | 119 | 118 | 117 | 116 | 115 | 114 | 113 | 112 | 111 | 110 |
| | 109 | 108 | 107 | 106 | 105 | 104 | 103 | 102 | 101 | 100 |
| | 99 | 98 | 97 | 96 | 95 | 94 | 93 | 92 | 91 | 90 |
| | 89 | 88 | 87 | 86 | 85 | 84 | 83 | 82 | 81 | 80 |
| | 79 | 78 | 77 | 76 | 75 | 74 | 73 | 72 | 71 | 70 |
| | 69 | 68 | 67 | 66 | 65 | 64 | 63 | 62 | 61 | 60 |
| | 59 | 58 | 57 | 56 | 55 | 54 | 53 | 52 | 51 | 50 |
| | 49 | 48 | 47 | 46 | 45 | 44 | 43 | 42 | 41 | 40 |
| | 39 | 38 | 37 | 36 | 35 | 34 | 33 | 32 | 31 | 30 |
| | 29 | 28 | 27 | 26 | 25 | 24 | 23 | 22 | 21 | 20 |
| | 19 | 18 | 17 | 16 | 15 | 14 | 13 | 12 | 11 | 10 |
| | 9 | 8 | 7 | 6 | 5 | 4 | 3 | 2 | 1 | 0 |
| | SAV4 | SAV4 | SAV4 | SAV4 | SAV4 | SAV4 | SAV4 | SAV4 | SAV4 | SAV4 |
| | SAV3 | SAV3 | SAV3 | SAV3 | SAV3 | SAV3 | SAV3 | SAV3 | SAV3 | SAV3 |
| | SAV2 | SAV2 | SAV2 | SAV2 | SAV2 | SAV2 | SAV2 | SAV2 | SAV2 | SAV2 |
| | SAV1 | SAV1 | SAV1 | SAV1 | SAV1 | SAV1 | SAV1 | SAV1 | SAV1 | SAV1 |
| | (a) | (b) | (c) | (d) | (e) | (f) | (g) | (h) | (i) | (j) |

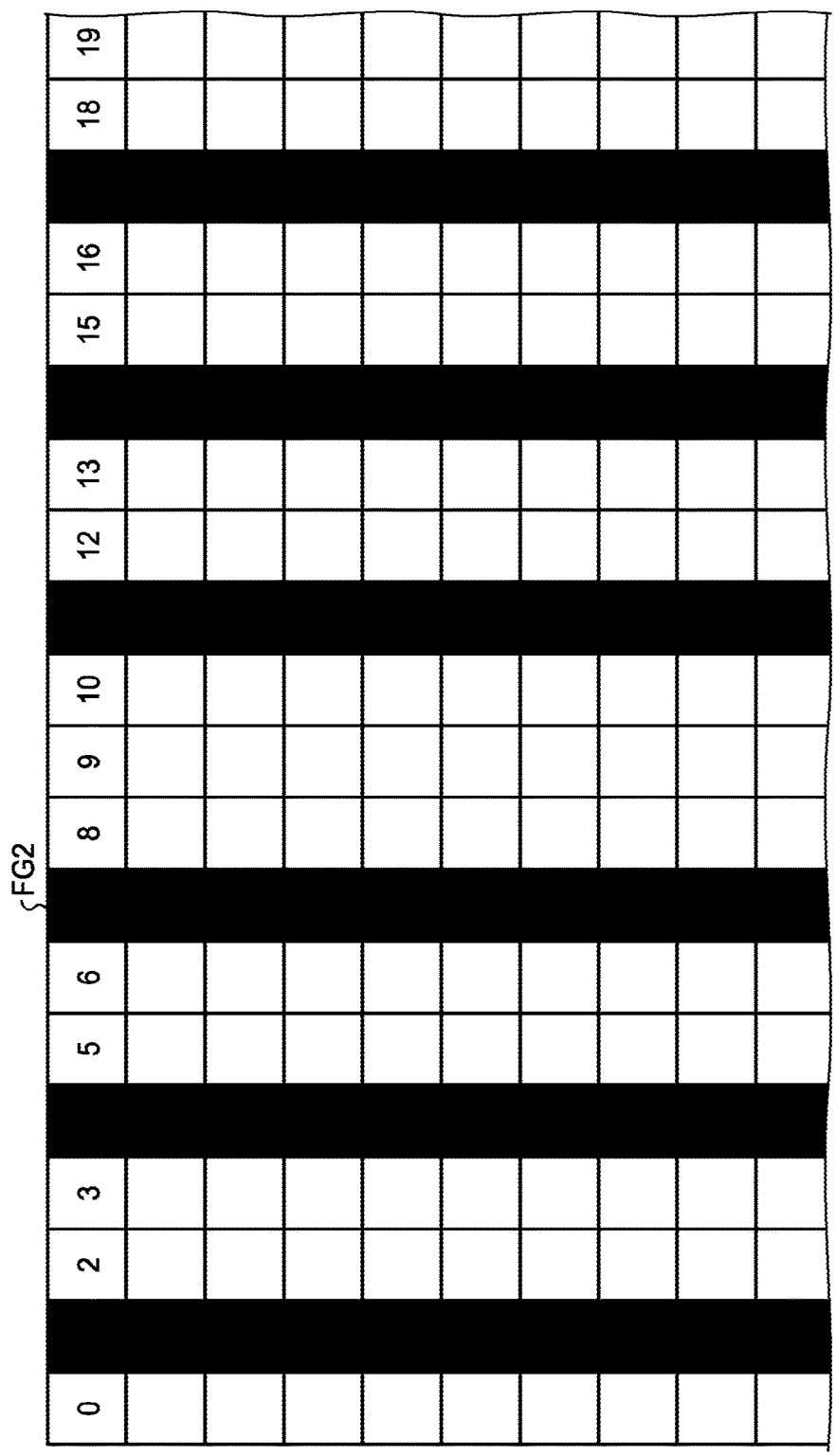

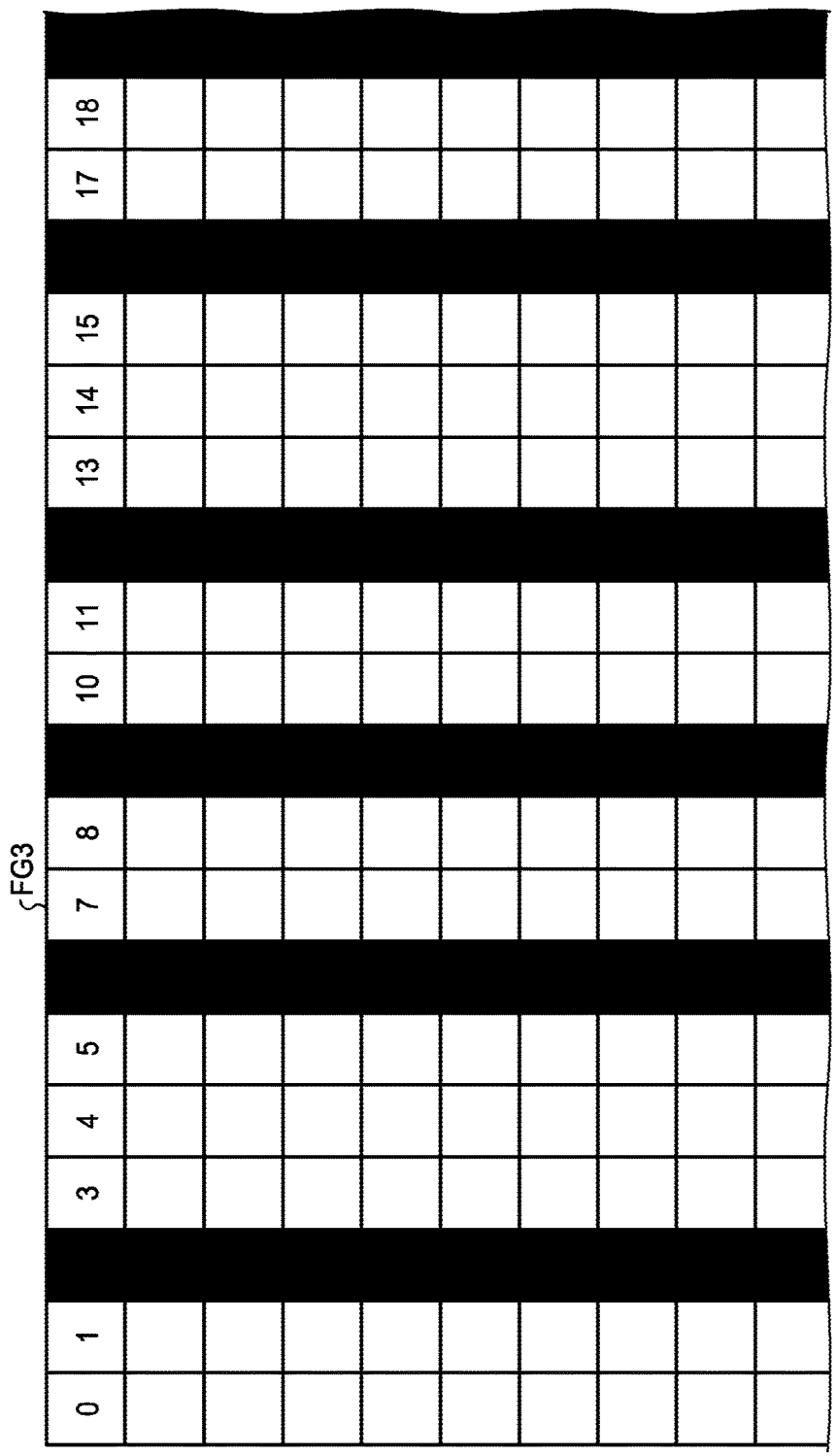

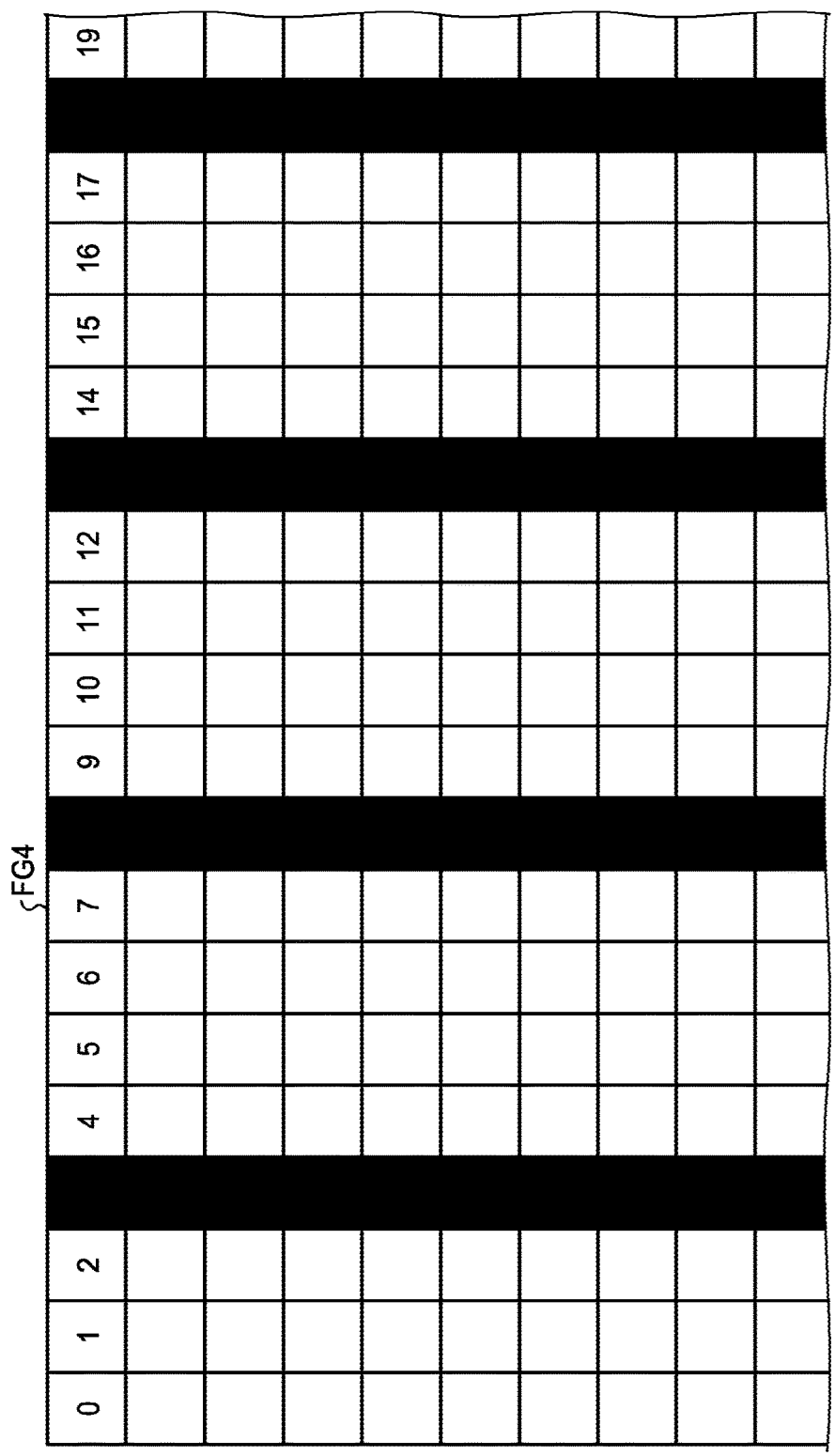

MEDICAL SIGNAL PROCESSING DEVICE AND MEDICAL OBSERVATION SYSTEM

CROSS-REFERENCE TO RELATED APPLICATION(S)

The present application claims priority to and incorporates by reference the entire contents of Japanese Patent Application No. 2016-006643 filed in Japan on Jan. 15, 2016.

BACKGROUND

The present disclosure relates to a medical signal processing device, and a medical observation system including the medical signal processing device.

Medical observation systems in the medical field are configured to capture an image of the inside of a subject such as a human (inside of a living body) to observe the inside of this living body (for example, refer to Japanese Patent Laid-open No. 2009-61032 and Japanese Patent Laid-open No. 2006-26134).

Medical observation systems disclosed in Japanese Patent Laid-open No. 2009-61032 and Japanese Patent Laid-open No. 2006-26134 ("electronic endoscope systems" in Japanese Patent Laid-open No. 2009-61032 and Japanese Patent Laid-open No. 2006-26134) each include a medical observation device ("electronic endoscope" in Japanese Patent Laid-open No. 2009-61032 and Japanese Patent Laid-open No. 2006-26134) configured to capture an image of the inside of a living body and output an image signal, a control device ("video processor" in Japanese Patent Laid-open No. 2009-61032 and "processor" in Japanese Patent Laid-open No. 2006-26134) configured to receive the image signal from the medical observation device and process the image signal to generate a display image signal, and a signal transmission path ("wireless connector" in Japanese Patent Laid-open No. 2009-61032 and "signal line" in Japanese Patent Laid-open No. 2006-26134) through which the image signal from the medical observation device is transmitted to the control device.

SUMMARY

When a failure occurs in transmission of the image signal due to, for example, breaking of the signal transmission path, the control device is unable to appropriately generate the display image signal and display an image suitable for observation.

In the medical observation system disclosed in Japanese Patent Laid-open No. 2009-61032, when a signal transmission state in the signal transmission path is detected and the detected transmission state is inappropriate for transmission, an operator is warned or notified by, for example, a buzzer. However, in the medical observation system disclosed in Japanese Patent Laid-open No. 2009-61032, an image suitable for observation may not be displayed until the signal transmission path is replaced by, for example, the operator in response to this warning or notification.

The medical observation system disclosed in Japanese Patent Laid-open No. 2006-26134 is provided with at least two signal transmission paths through which an identical image signal is transmitted. With this configuration, in the medical observation system disclosed in Japanese Patent Laid-open No. 2006-26134, when a transmission failure occurs in one of the signal transmission paths, the image signal may be transmitted to the control device through the other signal transmission path, which achieves continuous display of an image suitable for observation. However, one of the signal transmission paths is unnecessary when no transmission failure occurs. In other words, in the medical observation system disclosed in Japanese Patent Laid-open No. 2006-26134, the above-described signal transmission path needs to be redundantly provided, which prevents simplification of the structure.

It has been desired to achieve a technique of performing, with a simplified structure, continuous display of an image suitable for observation when a transmission failure occurs in a signal transmission path.

There is a need for a medical signal processing device and a medical observation system capable of performing, with a simplified structure, continuous display of an image suitable for observation when a transmission failure occurs in a signal transmission path.

According to one aspect of the present disclosure, there is provided a medical signal processing device for receiving an image signal in accordance with a result of examining inside of a subject and processing the image signal, wherein the image signal includes a plurality of pixel data groups of respective pixels arrayed at a constant interval among pixels sequentially arrayed in a predetermined direction in an image made of pixels arrayed in a matrix, the pixel data groups are data of respective pixels that are different from each other, the pixel data groups are input in the medical signal processing device in parallel, the medical signal processing device includes a distribution processing unit configured to generate a plurality of distributed image signals by combining, among the pixel data groups, pixel data groups of respective pixels that are separate from each other, and the distributed image signals are transmitted to an external medical control device through a plurality of respective signal transmission paths.

BRIEF DESCRIPTION OF THE DRAWINGS

FIG. 3A is a diagram illustrating an image signal output from an imaging unit illustrated in FIG. 2;

FIG. 3B is a diagram illustrating an image signal output from the imaging unit illustrated in FIG. 2;

FIG. 4 is a block diagram of the configuration of a transmission signal processing unit illustrated in FIG. 2;

FIG. 5 is a diagram illustrating first to tenth image signals after S/P conversion processing is executed by an S/P conversion unit illustrated in FIG. 4;

FIG. 6 is a diagram illustrating first to fourth distributed image signals generated by a distribution processing unit illustrated in FIG. 4;

FIG. 10B is a diagram illustrating the effect of the first embodiment of the present disclosure;

FIG. 10C is a diagram illustrating the effect of the first embodiment of the present disclosure;

FIG. 10D is a diagram illustrating the effect of the first embodiment of the present disclosure;

DETAILED DESCRIPTION

Figure 1:
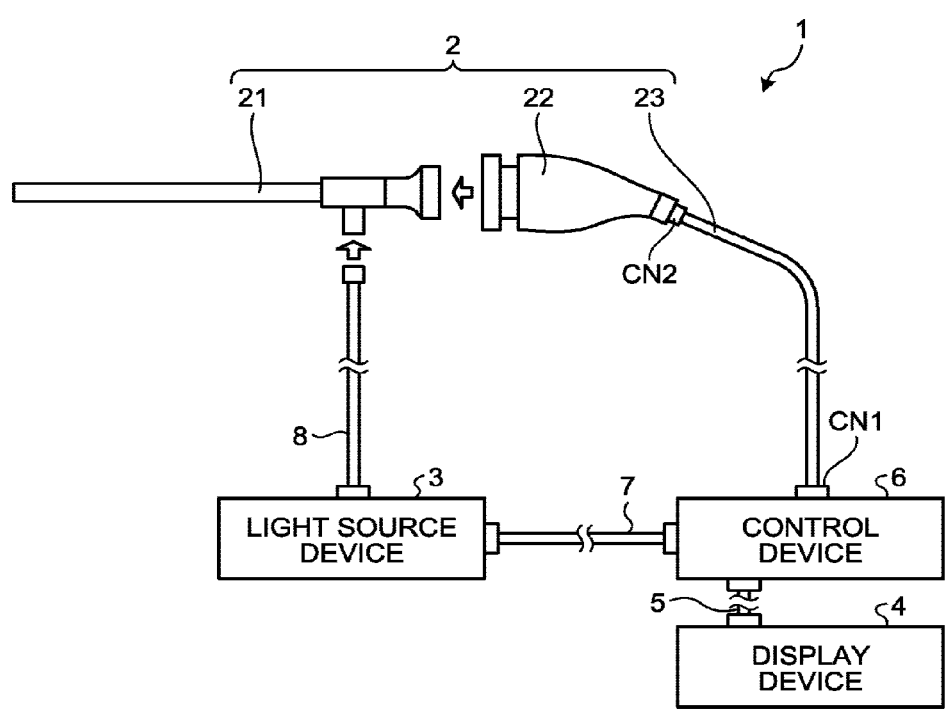
FIG. 1 is a diagram illustrating a schematic configuration of a medical observation system according to a first embodiment of the present disclosure.

Configurations to achieve the present disclosure (hereinafter referred to as embodiments) will be described below with reference to the accompanying drawings. The embodiments described below, however, are not intended to limit the present disclosure. In description of the drawings, any identical parts are denoted by an identical reference numeral.

First Embodiment

Schematic Configuration of Medical Observation System

FIG. 1 is a diagram illustrating a schematic configuration of a medical observation system 1 according to a first embodiment of the present disclosure.

The medical observation system 1 is used in the medical field to observe the inside of a subject such as a human (inside of a living body). As illustrated in FIG. 1, the medical observation system 1 includes an endoscope 2, a light source device 3, a display device 4, a second transmission cable 5, a control device 6, a third transmission cable 7, and a light guide 8.

The endoscope 2 examines the inside of the living body and outputs an image signal (a plurality of transmission image signals) in accordance with a result of this examination. As illustrated in FIG. 1, the endoscope 2 includes an insertion unit 21, a camera head 22, and a first transmission cable 23.

The insertion unit 21 is hard or at least partially soft, has an elongated shape, and is inserted into the inside of the living body. The insertion unit 21 includes an optical system that includes one or a plurality of lenses and through which an object image is condensed.

The light source device 3 is connected with one end of the light guide 8, and supplies, under control of the control device 6, this one end of the light guide 8 with light for illumination of the inside of the living body.

The light guide 8 has one end detachably connected with the light source device 3 and the other end detachably connected with the insertion unit 21. The light guide 8 transfers the light supplied by the light source device 3 from the one end to the other end to supply the light to the insertion unit 21. The light supplied to the insertion unit 21 is emitted from a leading end of the insertion unit 21 and incident on the inside of the living body. The light (object image) incident on the inside of the living body is condensed through the optical system in the insertion unit 21.

The camera head 22 is detachably connected with a base end of the insertion unit 21. The camera head 22 captures, under control of the control device 6, the object image condensed through the insertion unit 21 and generates an image capturing signal (image signal). The camera head 22 also generates a plurality of transmission image signals from this image signal and outputs these transmission image signals. In the first embodiment, the camera head 22 converts these transmission image signals into optical signals and outputs these transmission image signals as the optical signals.

The configuration of the camera head 22 will described later in detail.

The first transmission cable 23 has one end detachably connected with the control device 6 through a connector CN1 (FIG. 1) and the other end connected with the camera head 22 through a connector CN2 (FIG. 1). Specifically, the first transmission cable 23 includes a plurality of electric wires 231 (refer to FIG. 2) and a plurality of optical fibers 232 (refer to FIG. 2) arranged inside of an outer cover, which is an outermost layer.

Figure 2:
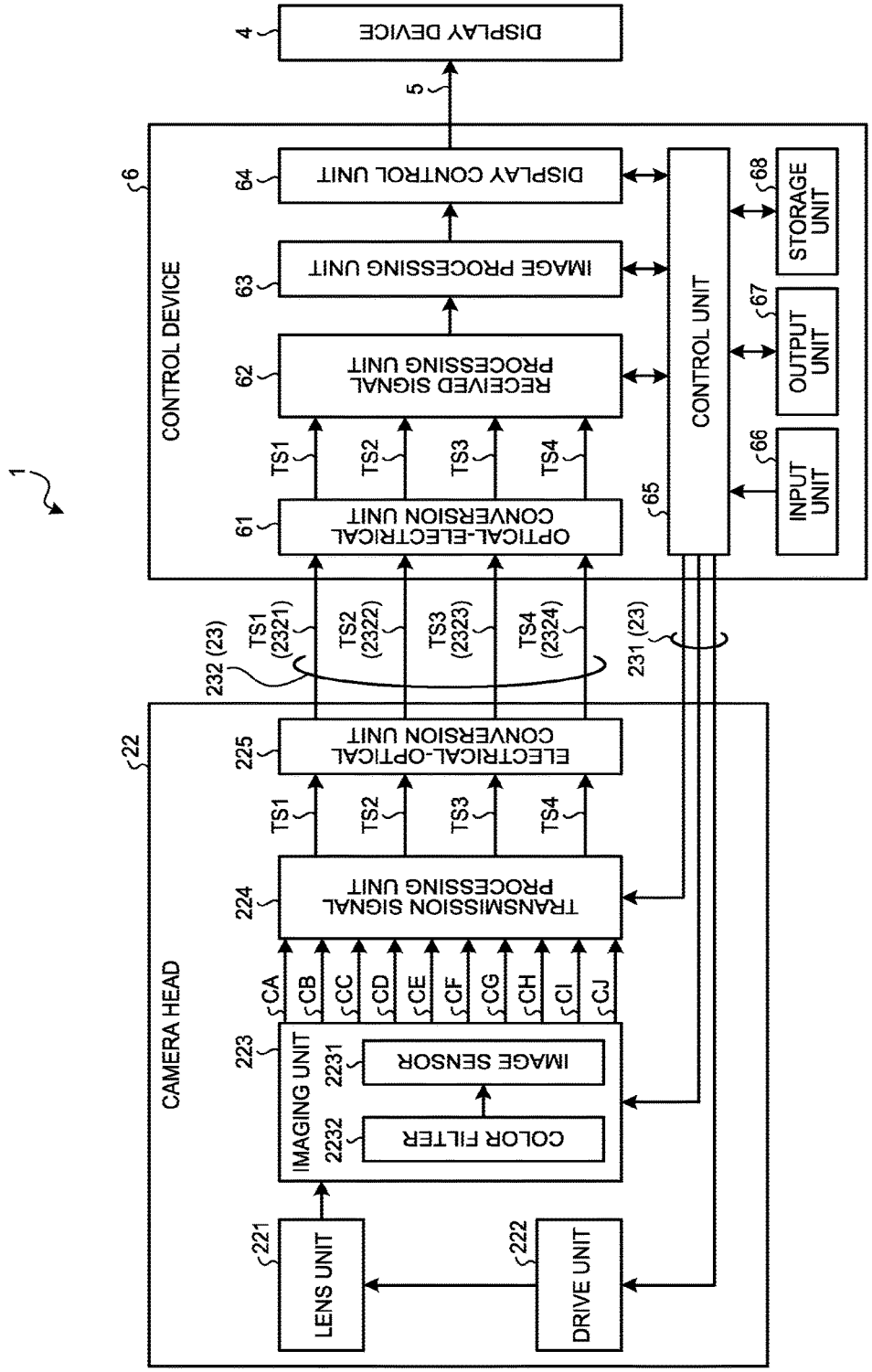
FIG. 2 is a block diagram of the configurations of a camera head and a control device illustrated in FIG. 1.

The electric wires 231 are electric wires for transmitting, for example, a control signal, a synchronizing signal, a clock, and electrical power output from the control device 6 to the camera head 22. In FIG. 2, the number of the electric wires 231 is three but not limited thereto, and may be any other number.

The optical fibers 232 are optical fibers for transmitting, to the control device 6, the transmission image signals (optical signals) output from the camera head 22. In the first embodiment, the four optical fibers 232 of first to fourth optical fibers 2321 to 2324 (refer to FIG. 2) are provided. The number of the provided optical fibers 232 depends on the number of optical signals output from the camera head 22 and is changed in accordance with any change in the number of optical signals.

The optical fibers 232 included in the first transmission cable 23 each function as a signal transmission path according to the present disclosure.

The display device 4 includes a display exploiting, for example, liquid crystal or organic electro luminescence (EL), and displays an image based on image signals processed at the control device 6.

The second transmission cable 5 has one end detachably connected with the display device 4 and the other end detachably connected with the control device 6. The second transmission cable 5 transmits image signals processed at the control device 6 to the display device 4.

The control device 6 includes, for example, a central processing unit (CPU) and performs overall control of operation of the light source device 3, the camera head 22, and the display device 4.

The configuration of the control device 6 will be described later in detail.

The third transmission cable 7 has one end detachably connected with the light source device 3 and the other end detachably connected with the control device 6. The third transmission cable 7 transmits, to the light source device 3, a control signal from the control device 6.

Configuration of Camera Head

The following describes the configuration of the camera head 22.

FIG. 2 is a block diagram of the configurations of the camera head 22 and the control device 6.

For the purpose of description, FIG. 2 omits illustrations of the connectors CN1 and CN2 connecting the control device 6 and the camera head 22 with the first transmission cable 23, and connectors connecting the control device 6 and the display device 4 with the second transmission cable 5.

As illustrated in FIG. 2, the camera head 22 includes a lens unit 221, a drive unit 222, an imaging unit 223, a transmission signal processing unit 224, and an electrical-optical conversion unit 225.

The lens unit 221 includes one or a plurality of lenses movable along an optical axis and images the object image condensed through the insertion unit 21 onto an imaging plane of the imaging unit 223 (an image sensor 2231 (FIG. 2)). The lens unit 221 is provided with an optical zoom mechanism (not illustrated) that changes an angle of view by moving the one or plurality of lenses, and a focus mechanism (not illustrated) that changes focus.

The drive unit 222 operates, under control of the control device 6, the optical zoom mechanism and the focus mechanism described above to change the angle of view and the focus of the lens unit 221.

The imaging unit 223 images the inside of the living body under control of the control device 6. The imaging unit 223 includes a sensor chip on which, for example, the image sensor 2231, such as a charge-coupled device (CCD) or a complementary metal oxide semiconductor (CMOS), configured to receive the object image condensed through the insertion unit 21 and imaged through the lens unit 221 and convert the object image into an electric signal, and a signal processing unit (not illustrated) configured to perform signal processing (such as A/D conversion) on the electric signal (analog signal) from the image sensor 2231 to output an image signal are integrally formed, and outputs the image signal (digital signal) after the A/D conversion. The signal processing unit (not illustrated) described above does not need to be formed integrally with the image sensor 2231 but may be formed separately.

The imaging plane (light-receiving surface) of the image sensor 2231 is provided thereon with a color filter 2232 (FIG. 2) in which filters sorted in three filter groups depending on a wavelength band (red (R), green (G), or blue (B)) of light to be transmitted are arrayed in a predetermined format (for example, a Bayer array).

More specifically, the color filter 2232 includes an R filter group through which light in the R wavelength band is transmitted, a B filter group through which light in the B wavelength band is transmitted, a first G filter group (arrayed in a column including the R filter group) through which light in the G wavelength band is transmitted, and a second G filter group (arrayed in a column including the B filter group) through which light in the G wavelength band is transmitted. Hereinafter, for the purpose of illustration, the first G filter group and the second G filter group are collectively referred to as a G filter group.

Accordingly, an image signal generated by the imaging unit 223 includes, for each pixel, any of R, G, and B component information (pixel data) corresponding to the respective R, G, and B filter groups.

In the first embodiment, the imaging unit 223 outputs the image signal after the A/D conversion through 10 channels (first to tenth channels CA to CJ (FIG. 2)) in parallel. The number of channels is not limited to 10 but may be any other number.

The image signal from the imaging unit 223 according to the first embodiment may be output as differential signals for the respective channels. In this case, for example, the signal processing unit (not illustrated) described above may be provided with a differential conversion unit (not illustrated) configured to convert the image signal after the A/D conversion into differential signals, and the transmission signal processing unit 224 to be described later may be provided with a restoring unit (not illustrated) configured to restore the differential signals to the original image signal.

FIGS. 3A and 3B are each a diagram illustrating the image signal output from the imaging unit 223. Specifically, FIG. 3A is a diagram illustrating a physical arrangement of effective pixels of the image sensor 2231. FIG. 3B is a diagram illustrating the image signal output from the imaging unit 223.

The number of bits per pixel in the image signal output from the imaging unit 223 is 10 in the first embodiment, but may be any other number.

In FIG. 3A, pixels on the first row are denoted by sequential numbers (address numbers of "0", "1", "2", . . . ) starting at the first column. Pixels at the second row are denoted by sequential address numbers (illustrated as, for example, a triangle in FIG. 3A) starting at the first column and following the address number of the pixel at the last column on the first row. The same notation applies to the third row and the following rows. In FIG. 3A, each pixel is denoted by such an address number followed by a reference sign ("CA" to "CJ") in parentheses, of any of the first to the tenth channels CA to CJ through which pixel data (any of R, G, and B component information corresponding to the respective R, G, and B filter groups (color filter 2232)) generated at this pixel is output. In addition, (a) to (j) in FIG. 3B illustrate pixel data (in FIG. 3B, for sake of simplicity, pixel data of pixels at address numbers "0" to "9") output through the first to the tenth channels CA to CJ. In FIG. 3B, an address number indicating a pixel at which pixel data is obtained is provided at each bit position of this pixel data, followed by this bit position (with a most significant bit (MSB; the bit position of a most significant digit) of "9" and a least significant bit (LSB; the bit position of a least significant digit) of "0" in parentheses.

In the first embodiment, as illustrated in FIGS. 3A and 3B, the imaging unit 223 converts pixel data generated at the pixel of address number "0" into serial data, and outputs the serial data bit by bit sequentially from the MSB through the first channel CA. The imaging unit 223 also converts pixel data generated at the pixel of address number "1" into serial data, and outputs the serial data bit by bit sequentially from the MSB through the second channel CB. Similarly, the imaging unit 223 converts each piece of pixel data generated at the pixels of address numbers "2" to "9" into serial data, and outputs the serial data bit by bit sequentially from the MSB through the third to the tenth channels CC to CJ.

In the pieces of pixel data vertically arranged in FIG. 3B, pieces of data at an identical bit position are output simultaneously through the first to the tenth channels CA to CJ, respectively.

Specifically, the imaging unit 223 outputs, in parallel through the first to the tenth channels CA to CJ as described above, pieces of pixel data (serial data) generated at 10 pixels each in an order of the address number.

In the first embodiment, as illustrated in FIG. 3A, pieces of pixel data generated at pixels at an identical column are output through an identical channel.

Although not illustrated in FIGS. 3A and 3B, the imaging unit 223 outputs timing reference codes "SAV1" to "SAV4" made of four words (one word=10 bits) in parallel through the first to the tenth channels CA to CJ (refer to FIG. 5) before outputting, in parallel through the first to the tenth channels CA to CJ, pieces of pixel data (serial data) generated at 10 pixels each in an order of the address number. After outputting, in parallel through the first to the tenth channels CA to CJ, the pieces of pixel data (serial data) generated at 10 pixels each in an order of the address number, the imaging unit 223 outputs timing reference codes "EAV1" to "EAV4" made of four words (one word=10 bits) in parallel through the first to the tenth channels CA to CJ (refer to FIG. 5).

The image signals output in parallel through the first to the tenth channels CA to CJ described above correspond to the pixel data groups according to the present disclosure.

FIG. 4 is a block diagram of the configuration of the transmission signal processing unit 224.

In FIG. 4, the flow of a signal output in parallel data is illustrated by an arrow intersected with a diagonal line. The same notation applies to FIG. 2 and the following figures.

The transmission signal processing unit 224 functions as a medical signal processing device according to the present disclosure and executes, on the image signal (in 10 bits through 10 channels) from the imaging unit 223, various kinds of processing such as S/P conversion processing, transmission image signal generation processing (mapping processing and auxiliary data addition processing), encoding processing (N bit/M (>N) bit conversion processing (in the first embodiment, 8 bits/10 bits conversion processing)), and P/S conversion processing. As illustrated in FIG. 4, the transmission signal processing unit 224 includes an S/P conversion unit 226, a signal processing unit 227, and a plurality of drivers 228.

The S/P conversion unit 226 executes the S/P conversion processing on the image signal (serial data in 10 bits through 10 channels) output from the imaging unit 223 and converts the image signal into parallel data.

FIG. 5 is a diagram illustrating first to tenth image signals FS1 to FS10 (parallel data) after the S/P conversion processing is executed at the S/P conversion unit 226.

Numbers ("0" to "4249") illustrated in FIG. 5 correspond to the address numbers illustrated in FIG. 3A and each indicate pixel data (10 bits) generated at a pixel of the corresponding address number. Pixel data generated at the pixels of address numbers "0" to "4249" is effective data (pixel data obtained in an effective image region).

Specifically, as illustrated in (a) in FIG. 5, the S/P conversion unit 226 generates the first image signal FS1 (parallel data) by executing the S/P conversion processing on an image signal (the timing reference codes "SAV1" to "SAV4" and "EAV1" to "EAV4", and pieces of pixel data (pieces of pixel data generated at the pixels of address numbers "0", "10", "20", . . . )) output through the first channel CA. As illustrated in (b) in FIG. 5, the S/P conversion unit 226 also generates the second image signal FS2 (parallel data) by executing the S/P conversion processing on an image signal (the timing reference codes "SAV1" to "SAV4" and "EAV1" to "EAV4", and pieces of pixel data (pieces of pixel data generated at the pixels of address numbers "1", "11", "21", . . . )) output through the second channel CB. Similarly, as illustrated in (c) to (j) in FIG. 5, the S/P conversion unit 226 generates the third to the tenth image signals FS3 to FS10 (parallel data) by executing the S/P conversion processing on image signals output through the third to the tenth channels CC to CJ.

In the first embodiment, address numbers of "0" to "4249" are provided and thus the number of pixels in the effective image region of the image sensor 2231 is 4250, but the present disclosure is not limited thereto. The number of pixels in the effective image region of an image sensor in use may be changed to any other number as appropriate.

The signal processing unit 227 generates a plurality of transmission image signals by executing the transmission signal generation processing (the mapping processing and the auxiliary data addition processing) on the first to the tenth image signals FS1 to FS10 (parallel data) generated at the S/P conversion unit 226.

In the first embodiment, as illustrated in FIG. 4, the signal processing unit 227 generates four of first to fourth transmission image signals TS1 to TS4 from the first to the tenth image signals FS1 to FS10. The number of transmission image signals is not limited to four but may be any other number.

As illustrated in FIG. 4, the signal processing unit 227 includes a distribution processing unit 2271 and a data addition unit 2272.

The distribution processing unit 2271 generates four of first to fourth distributed image signals DS1 to DS4 by distributing (executes the mapping processing on) the first to the tenth image signals FS1 to FS10 (parallel data) generated at the S/P conversion unit 226.

Figure 7:
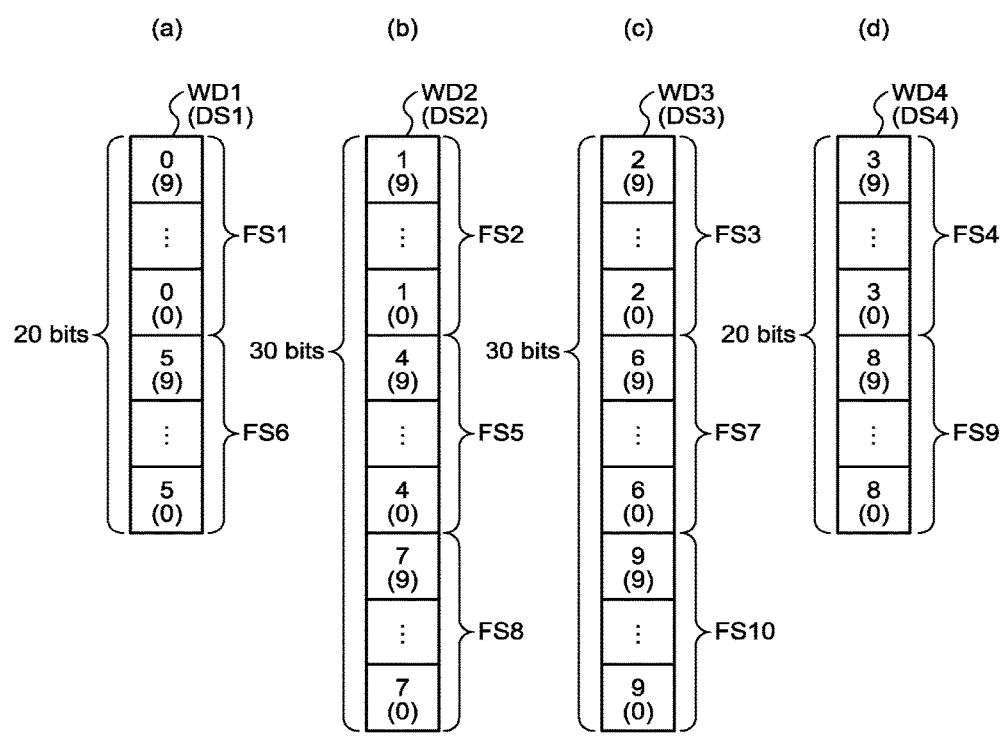
FIG. 7 is a diagram illustrating the first to the fourth distributed image signals generated by the distribution processing unit illustrated in FIG. 4.

FIGS. 6 and 7 are diagrams illustrating the first to the fourth distributed image signals DS1 to DS4 generated at the distribution processing unit 2271. Specifically, FIG. 6 corresponds to FIG. 5. (a) to (d) in FIG. 7 illustrate bit strings of the words WD1 to WD4 illustrated in (a) to (d) in FIG. 6, respectively.

In (a) to (d) in FIG. 7, each bit in the words WD1 to WD4 is denoted by an address number indicating the pixel of the corresponding pixel data, followed by a bit position in this pixel data in parentheses.

Specifically, as illustrated in FIGS. 6 and 7, the distribution processing unit 2271 distributes the first to the tenth image signals FS1 to FS10 into four signals by combining image signals of pixels that are separate from each other among the first to the tenth image signals FS1 to FS10 (in 10 bits through 10 channels). In the first embodiment, the distribution processing unit 2271 combines image signals of pixels that are separate from each other with at least two pixels interposed therebetween among the first to the tenth image signals FS1 to FS10.

For example, the first image signal FS1 includes pieces of pixel data generated at the pixels of address numbers "0", "10", "20", . . . . The second image signal FS2 includes pieces of pixel data generated at the pixels of address numbers "1", "11", "21", . . . . Thus, the first and the second image signals FS1 and FS2 are image signals of pixels (address numbers) that are adjacent to each other. The sixth image signal FS6 includes pieces of pixel data generated at the pixels of address numbers "5", "15", "25", . . . . Thus, the first and the sixth image signals FS1 and FS6 are image signals of pixels (address numbers) that are separate from each other with four pixels interposed therebetween.

Accordingly, as illustrated in (a) in FIG. 6 and (a) in FIG. 7, the first distributed image signal DS1 obtained through the distribution at the distribution processing unit 2271 is a signal (20 bits) as a combination of the first image signal FS1 (10 bits) and the sixth image signal FS6 (10 bits), which is separate from the first image signal FS1 with four pixels interposed therebetween. As illustrated in (b) in FIG. 6 and (b) in FIG. 7, the second distributed image signal DS2 is a signal (30 bits) as a combination of the second image signal FS2 (10 bits), the fifth image signal FS5 (10 bits), which is separate from the second image signal FS2 with two pixels interposed therebetween, and the eighth image signal FS8 (10 bits), which is separate from the fifth image signal FS5 with two pixels interposed therebetween and from the second image signal FS2 with three pixels interposed therebetween. As illustrated in (c) in FIG. 6 and (c) in FIG. 7, the third distributed image signal DS3 is a signal (30 bits) as a combination of the third image signal FS3 (10 bits), the seventh image signal FS7 (10 bits), which is separate from the third image signal FS3 with three pixels interposed therebetween, and the tenth image signal FS10 (10 bits), which is separate from the seventh image signal FS7 with two pixels interposed therebetween and from the third image signal FS3 with two pixels interposed therebetween. As illustrated in (d) in FIG. 6 and (d) in FIG. 7, the fourth distributed image signal DS4 is a signal (20 bits) as a combination of the fourth image signal FS4 (10 bits) and the ninth image signal FS9 (10 bits), which is separate from the fourth image signal FS4 with four pixels interposed therebetween.

In the first embodiment, the first to the tenth image signals FS1 to FS10 in 10 channels are distributed into the four of the first to the fourth distributed image signals DS1 to DS4 in units of channels, and thus the amount of data per word is not constant between the first to the fourth distributed image signals DS1 to DS4 (the first distributed image signal DS1: 20 bits, the second distributed image signal DS2: 30 bits, the third distributed image signal DS3: 30 bits, and the fourth distributed image signal DS4: 20 bits). However, the amount of data per word may be constant, instead of not being constant, between distributed image signals when the number of channels of an image signal input in the distribution processing unit 2271 and the number of distributed image signals obtained through the distribution at the distribution processing unit 2271 are set to different from those described above.

The data addition unit 2272 generates the first to the fourth transmission image signals TS1 to TS4 by adding auxiliary data to each of the four of the first to the fourth distributed image signals DS1 to DS4 to enable execution of the 8 bits/10 bits conversion processing at a later stage (by executing the auxiliary data addition processing).

In the first embodiment, the data addition unit 2272 adds auxiliary data of 12 bits per word to the first distributed image signal DS1 (20 bits). The data addition unit 2272 adds auxiliary data of two bits per word to the second distributed image signal DS2 (30 bits). The data addition unit 2272 adds auxiliary data of two bits per word to the third distributed image signal DS3 (30 bits). The data addition unit 2272 adds auxiliary data of 12 bits per word to the fourth distributed image signal DS4 (20 bits).

The auxiliary data added to the first to the fourth distributed image signals DS1 to DS4 may be any data that allows execution of the 8 bits/10 bits conversion processing at a later stage.

The drivers 228 are provided in accordance with the number of transmission image signals generated at the signal processing unit 227. Specifically, in the first embodiment, as illustrated in FIG. 4, the four drivers 228 of first to fourth drivers 2281 to 2284 are provided. The four of the first to the fourth drivers 2281 to 2284 execute the encoding processing (in the first embodiment, the 8 bits/10 bits conversion processing) on the first to the fourth transmission image signals TS1 to TS4 generated at the signal processing unit 227. The four of the first to the fourth drivers 2281 to 2284 execute the P/S conversion processing on the first to the fourth transmission image signals TS1 to TS4 after the encoding processing to convert the signals into serial data. Although not specifically illustrated, a clock signal is superimposed on this serial data, and, for example, a K code indicating the start position and the end position of effective data is inserted into the serial data.

The transmission signal processing unit 224 described above is achieved by a programmable logic device such as a field-programmable gate array (FPGA).

The electrical-optical conversion unit 225 converts the first to the fourth transmission image signals TS1 to TS4 (serial data) output from the transmission signal processing unit 224 (the four of the first to the fourth drivers 2281 to 2284) into optical signals, and outputs the optical signals to the first transmission cable 23 (the first to the fourth optical fibers 2321 to 2324). Then, the first to the fourth optical fibers 2321 to 2324 transmit the first to the fourth transmission image signals TS1 to TS4 to the control device 6.

Configuration of Control Device

The following describes the configuration of the control device 6 with reference to FIG. 2.

As illustrated in FIG. 2, the control device 6 includes an optical-electrical conversion unit 61, a received signal processing unit 62, an image processing unit 63, a display control unit 64, a control unit 65, an input unit 66, an output unit 67, and a storage unit 68.

The optical-electrical conversion unit 61 converts the four optical signals (the four of the first to the fourth transmission image signals TS1 to TS4) received through the first to the fourth optical fibers 2321 to 2324 into electric signals (serial data).

Figure 8:
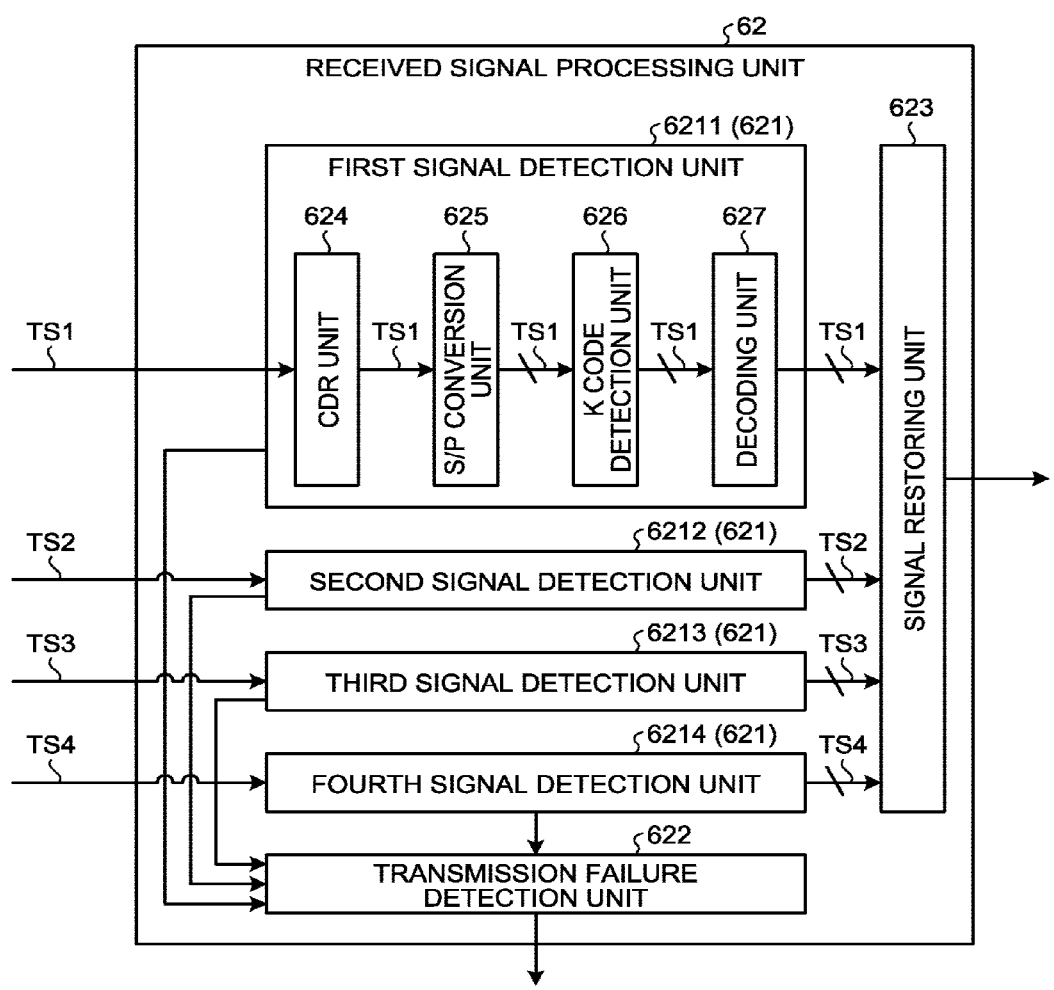
FIG. 8 is a block diagram of the configuration of a received signal processing unit illustrated in FIG. 2.

FIG. 8 is a block diagram of the configuration of the received signal processing unit 62.

The received signal processing unit 62 functions as a medical control device according to the present disclosure and executes, on the four pieces of serial data (the four of the first to the fourth transmission image signals TS1 to TS4) output from the optical-electrical conversion unit 61, various kinds of processing such as transmission failure detection processing, the S/P conversion processing, decoding processing (M bit/N (<M) bit conversion processing (in the first embodiment, 10 bits/8 bits conversion processing)), mapping decoding processing, and the P/S conversion processing. As illustrated in FIG. 8, the received signal processing unit 62 includes a plurality of signal detection units 621, a transmission failure detection unit 622, and a signal restoring unit 623.

The signal detection units 621 are provided in accordance with the number of optical fibers 232 (the first to the fourth transmission image signals TS1 to TS4) included in the first transmission cable 23. Specifically, in the first embodiment, the four signal detection units 621 are provided. Hereinafter, the signal detection units 621 corresponding to the first to the fourth transmission image signals TS1 to TS4 are referred to as first to fourth signal detection units 6211 to 6214, respectively (FIG. 8). The first to the fourth signal detection units 6211 to 6214 have an identical configuration, and thus only the configuration of the first signal detection unit 6211 corresponding to the first transmission image signal TS1 will be described below. For the purpose of description, FIG. 8 only illustrates a specific configuration of the first signal detection unit 6211, whereas specific configurations of the second to the fourth signal detection units 6212 to 6214 are omitted in the illustration.

As illustrated in FIG. 8, the first signal detection unit 6211 includes a clock recovery (CDR) unit 624, an S/P conversion unit 625, a K code detection unit 626, and a decoding unit 627.

The CDR unit 624 executes CDR processing that recovers the superimposed clock signal from the first transmission image signal TS1 (serial data) input to the optical-electrical conversion unit 61 through the optical fiber 232 (first optical fiber 2321) and converted at the optical-electrical conversion unit 61. Then, when the execution of the CDR processing is successful (the recovery of the superimposed clock signal is successful), the CDR unit 624 outputs processing execution information indicating the successful execution to the transmission failure detection unit 622. When the execution of the CDR processing is failed, the CDR unit 624 outputs, to the transmission failure detection unit 622, failed execution information indicating the failure, and identification information for identifying the optical fiber 232 (first optical fiber 2321) corresponding to the CDR unit 624.

The S/P conversion unit 625 executes the S/P conversion processing on the first transmission image signal TS1 (serial data) after the CDR processing to convert the signal into parallel data.

The K code detection unit 626 detects the K code from the first transmission image signal TS1 (parallel data) after the S/P conversion processing at the S/P conversion unit 625 to perform timing detection of data, and executes K code detection processing that acquires the effective data from the first transmission image signal TS1 (parallel data). Then, when the execution of the K code detection processing is successful (the acquisition of the effective data is successful), the K code detection unit 626 outputs processing execution information indicating the successful execution to the transmission failure detection unit 622. When the execution of the K code detection processing is failed, the K code detection unit 626 outputs, to the transmission failure detection unit 622, failed execution information indicating the failure, and identification information for identifying the optical fiber 232 (first optical fiber 2321) corresponding to the K code detection unit 626.

In the first embodiment, the K code detection unit 626 is employed, but the present disclosure is not limited thereto. When information other than the K code is inserted into the first to the fourth transmission image signals TS1 to TS4 by the camera head 22, a component having a function of detecting this information (component that outputs, to the transmission failure detection unit 622, for example, whether this information may be detected) may be employed.

The decoding unit 627 executes the decoding processing (in the first embodiment, 10 bits/8 bits conversion processing) on the first transmission image signal TS1 (effective data (parallel data) acquired at the K code detection unit 626) after the K code detection processing at the K code detection unit 626.

The transmission failure detection unit 622 detects any failure of transmission of optical signals through the first to the fourth optical fibers 2321 to 2324 based on the information output from the first to the fourth signal detection units 6211 to 6214 (the CDR unit 624 and the K code detection unit 626), and specifies an optical fiber in which a transmission failure has occurred.

Specifically, the first to the fourth signal detection units 6211 to 6214 and the transmission failure detection unit 622 execute the transmission failure detection processing to detect any failure of transmission of optical signals through the first to the fourth optical fibers 2321 to 2324, and specifies an optical fiber in which the transmission failure has occurred.

Then, the transmission failure detection unit 622 outputs transmission failure information (information indicating whether a transmission failure has occurred, and when a transmission failure occurs, an optical fiber in which this transmission failure has occurred) to the control unit 65.

The signal restoring unit 623 restores image signals (the first to the tenth image signals FS1 to FS10 (parallel data)) before the mapping processing at the camera head 22, by executing the mapping decoding processing on the first to the fourth transmission image signals TS1 to TS4 (parallel data) after the decoding processing at the decoding units 627 in the first to the fourth signal detection units 6211 to 6214.

Specifically, the signal restoring unit 623 extracts the first to the fourth distributed image signals DS1 to DS4, respectively, from the first to the fourth transmission image signals TS1 to TS4 after the decoding processing at the decoding units 627 in the first to the fourth signal detection units 6211 to 6214. Then, the signal restoring unit 623 restores image signals (the first to the tenth image signals FS1 to FS10) before the mapping processing at the camera head 22, by executing the inverse processing (the mapping decoding processing) of the mapping processing at the camera head 22 on these extracted first to fourth distributed image signals DS1 to DS4.

When a transmission failure occurs in any of the first to the fourth optical fibers 2321 to 2324, a transmission image signal (distributed image signal) corresponding to an optical fiber in which this transmission failure has occurred is lost (has no pixel data). Specifically, when a transmission failure occurs in the first optical fiber 2321, the first distributed image signal DS1 is lost, and thus the first and the sixth image signals FS1 and FS6 among the first to the tenth image signals FS1 to FS10 restored by the signal restoring unit 623 are lost. When a transmission failure occurs in the second optical fiber 2322, the second distributed image signal DS2 is lost, and thus the second, the fifth, and the eighth image signals FS2, FS4, and FS8 among the first to the tenth image signals FS1 to FS10 restored by the signal restoring unit 623 are lost. When a transmission failure occurs in the third optical fiber 2323, the third distributed image signal DS3 is lost, and thus the third, the seventh, and the tenth image signals FS3, FS7, and FS10 among the first to the tenth image signals FS1 to FS10 restored by the signal restoring unit 623 are lost. When a transmission failure occurs in the fourth optical fiber 2324, the fourth distributed image signal DS4 is lost, and thus the fourth and the ninth image signals FS4 and FS9 among the first to the tenth image signals FS1 to FS10 restored by the signal restoring unit 623 are lost.

Similarly to the transmission signal processing unit 224, the received signal processing unit 62 described above is achieved by a programmable logic device such as a FPGA.

The image processing unit 63 executes, on an image signal (serial data) restored by the received signal processing unit 62, various kinds of image processing such as development processing (demosaic processing), noise reduction, color correction, color enhancement, and outline enhancement. When a transmission failure is detected by the transmission failure detection unit 622, the image processing unit 63 executes image processing described below.

Figure 9:
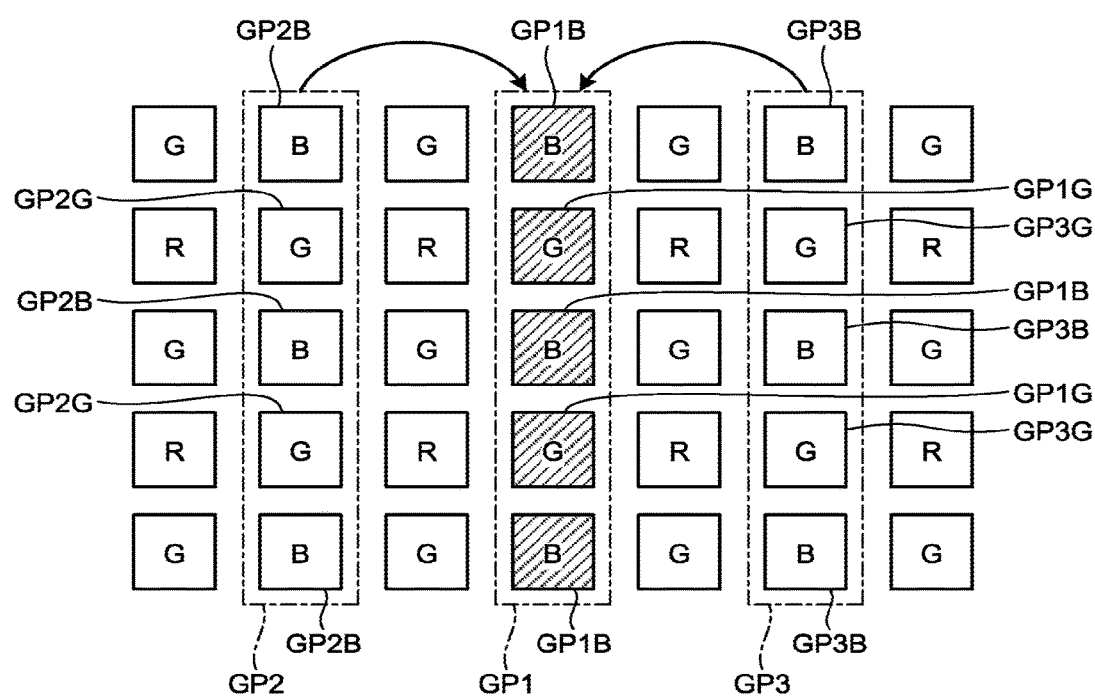
FIG. 9 is a diagram of exemplary image processing by an image processing unit illustrated in FIG. 2, illustrating image processing executed when a transmission failure is detected by a transmission failure detection unit.

FIG. 9 is a diagram of exemplary image processing by the image processing unit 63, illustrating image processing when a transmission failure is detected by the transmission failure detection unit 622. Specifically, FIG. 9 is a diagram illustrating an image in accordance with image signals restored by the signal restoring unit 623.

In FIG. 9, for the purpose of illustration, the character of "R" is attached to a pixel corresponding to the R filter group in the color filter 2232, the character of "G" is attached to a pixel corresponding to the G filter group, and the character of "B" is attached to a pixel corresponding to the B filter group. In FIG. 9, a pixel group GP1 lost due to a transmission failure in any of the first to the fourth optical fibers 2321 to 2324 is hatched.

When a transmission failure is detected by the transmission failure detection unit 622, as illustrated in FIG. 9, the image processing unit 63 compensates for each pixel data (component information) of the lost pixel group GP1 based on pixel data (component information) of two pixel groups GP2 and GP3 that are separate from this pixel group GP1 with one pixel interposed therebetween.

Specifically, as illustrated in FIG. 9, the image processing unit 63 compensates for pixel data of a pixel GP1B corresponding to the B filter group in the pixel group GP1 with pixel data obtained by averaging pixel data of two other pixels GP2B and GP3B (pixels corresponding to the B filter group in the pixel groups GP2 and GP3) that are adjacent to the pixel GP1B among pixels corresponding to the B filter group of the pixel GP1B. The image processing unit 63 compensates for pixel data of a pixel GP1G corresponding to the G filter group in the pixel group GP1 with pixel data obtained by averaging pixel data of two other pixels GP2G and GP2G (pixels corresponding to the G filter group in the pixel groups GP2 and GP3) that are adjacent to the pixel GP1G among pixels corresponding to the G filter group of the pixel GP1G.

In FIG. 9, the pixel group GP1 does not include a pixel corresponding to the R filter group. When this pixel group GP1 includes a pixel corresponding to the R filter group, however, the image processing unit 63 compensates for pixel data of this pixel in the same manner based on pixel data of two pixels corresponding to the R filter group that is separate from this pixel with one pixel interposed therebetween.

The display control unit 64 generates a display image signal from the image signal (serial data) after the various kinds of image processing at the image processing unit 63, and outputs the display image signal to the display device 4 through the second transmission cable 5. Then, the display device 4 displays an image (hereinafter referred to as an observation image) based on this display image signal. When a transmission failure is detected by the transmission failure detection unit 622, the display control unit 64 generates an image signal for displaying, on the display device 4, a superimposed image obtained by superimposing, on the observation image, for example, a message indicating the occurrence of the transmission failure and a message indicating an optical fiber in which the transmission failure has occurred, and outputs the image signal to the display device 4 through the second transmission cable 5. Then, the display device 4 displays the superimposed image (image in which the messages are superimposed on the observation image) based on this image signal.

In other words, the display device 4 functions as a notification unit according to the present disclosure. The display control unit 64 functions as a notification control unit according to the present disclosure.

The control unit 65 includes, for example, a CPU, and controls operation of the light source device 3, the drive unit 222, the imaging unit 223, and the transmission signal processing unit 224 and operation of the entire control device 6 by outputting control signals through the third transmission cable 7 and the electric wires 231.

The input unit 66 includes an operation device such as a mouse, a keyboard, or a touch panel to receive an operation by a user.

The output unit 67 includes, for example, a speaker and a printer to output various kinds of information. When a transmission failure is detected by the transmission failure detection unit 622, the output unit 67 outputs sound indicating the occurrence of the transmission failure, and sound indicating an optical fiber in which the transmission failure has occurred.

In other words, the output unit 67 functions as the notification unit according to the present disclosure. The control unit 65 functions as the notification control unit according to the present disclosure.

The notification unit according to the present disclosure is not limited to the display device 4 and the output unit 67, but may be, for example, an LED that gives notification of predetermined information by lighting or flashing.

The medical observation system 1 according to the first embodiment described above achieves an effect described below.

FIGS. 10A to 10D are each a diagram illustrating the effect of the first embodiment of the present disclosure. Specifically, FIGS. 10A to 10D are diagrams of respective observation images FG1 to FG4 displayed on the display device 4 when a transmission failure occurs in any of the first to the fourth optical fibers 2321 to 2324, illustrating a case in which the image processing unit 63 does not execute the image processing illustrated in FIG. 9 (the image processing unit 63 does not compensate for pixel data of the lost pixel group GP1).

In FIGS. 10A to 10D, for the purpose of illustration, the address number (FIG. 3A) corresponding to each pixel at the image sensor 2231 is attached to part of the observation images FG1 to FG4.

In the medical observation system 1 according to the first embodiment, the first to the tenth image signals FS1 to FS10 are distributed into the four of the first to the fourth distributed image signals DS1 to DS4 by combining image signals of pixels that are separate from each other with at least two pixels interposed therebetween among the first to the tenth image signals FS1 to FS10 in units of channels of the first to the tenth image signals FS1 to FS10.

The first distributed image signal DS1 is a combination of the first image signal FS1 including pieces of pixel data generated at the pixels of address numbers "0", "10", "20", . . . , and the sixth image signal FS6 including pieces of pixel data generated at the pixels of address numbers "5", "15", "25", . . . .

Figure 10A:
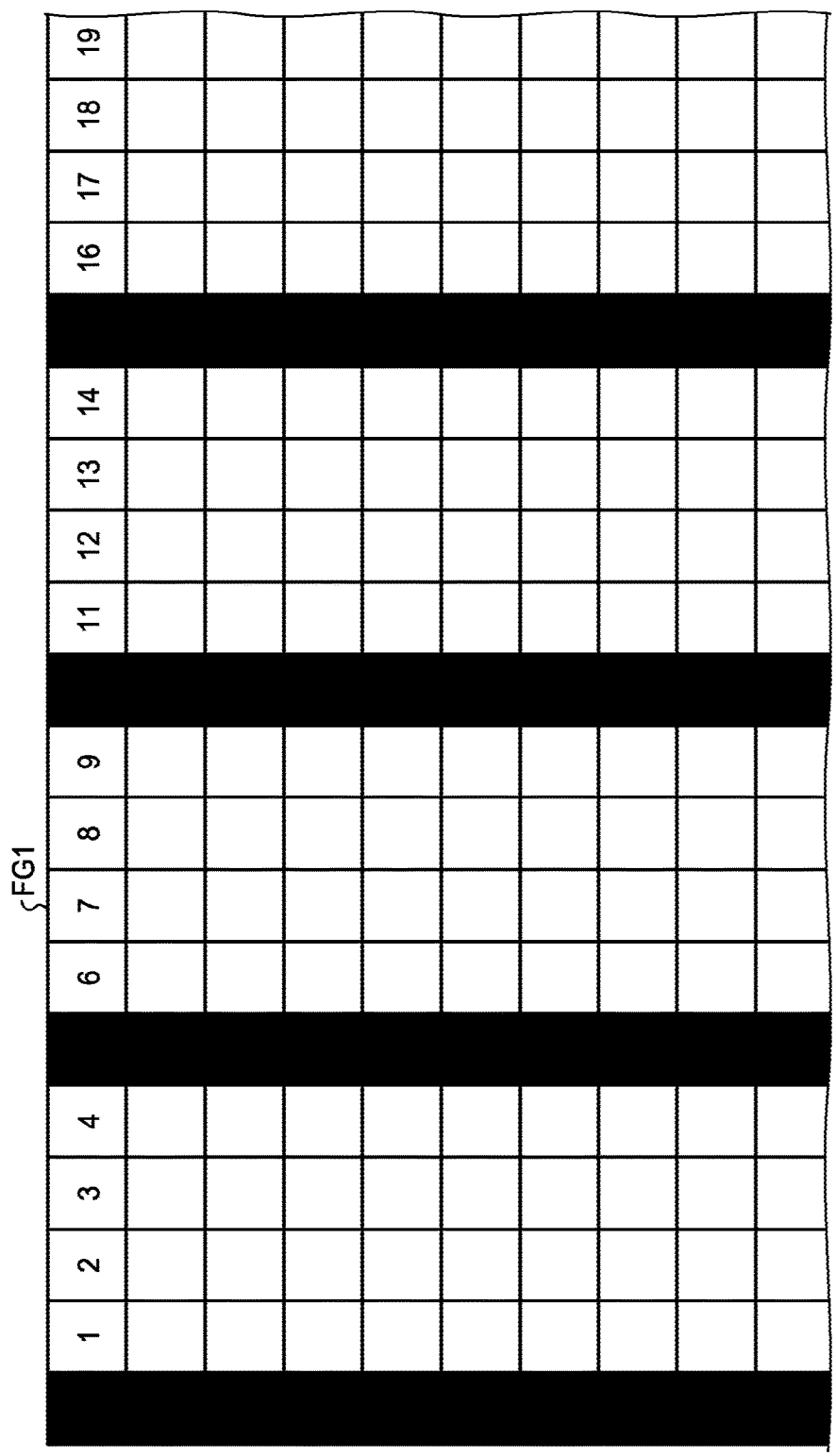
FIG. 10A is a diagram illustrating an effect of the first embodiment of the present disclosure.

Thus, when a transmission failure occurs in the first optical fiber 2321, in the observation image FG1 displayed on the display device 4, an image loss occurs on vertical lines of the first column, the eleventh column, . . . (the pixels of address numbers "0", "10", "20", . . . ) corresponding to the first image signal FS1 along with a loss of the first image signal FS1 as illustrated in FIG. 10A. In addition, in the observation image FG1, an image loss occurs on vertical lines of the sixth column, the sixteenth column, . . . (the pixels of address numbers "5", "15", "25", . . . ) corresponding to the sixth image signal FS6 along with a loss of the sixth image signal FS6.

The second distributed image signal DS2 is a combination of the second image signal FS2 including pieces of pixel data generated at the pixels of address numbers "1", "11", "21", . . . , the fifth image signal FS5 including pieces of pixel data generated at the pixels of address numbers "4", "14", "24", . . . , and the eighth image signal FS8 including pieces of pixel data generated at the pixels of address numbers "7", "17", "27", . . . .

Thus, when a transmission failure occurs in the second optical fiber 2322, in the observation image FG2 displayed on the display device 4, an image loss occurs on vertical lines of the second column, the twelfth column, . . . (the pixels of address numbers "1", "11", "21", . . . ) corresponding to the second image signal FS2 along with a loss of the second image signal FS2 as illustrated in FIG. 10B. In addition, in the observation image FG2, an image loss occurs on vertical lines of the fifth column, the fifteenth column, . . . (the pixels of address numbers "4", "14", "24", . . . ) corresponding to the fifth image signal FS5 along with a loss of the fifth image signal FS5. In addition, in the observation image FG2, an image loss occur on vertical lines of the eighth column, the eighteenth column, . . . (the pixels of address numbers "7", "17", "27", . . . ) corresponding to the eighth image signal FS8 along with a loss of the eighth image signal FS8.

The third distributed image signal DS3 is a combination of the third image signal FS3 including pieces of pixel data generated at the pixels of address numbers "2", "12", "22", . . . , the seventh image signal FS7 including pieces of pixel data generated at the pixels of address numbers "6", "16", "26", . . . , and the tenth image signal FS10 including pieces of pixel data generated at the pixels of address numbers "9", "19", "29", . . . .

Thus, when a transmission failure occurs in the third optical fiber 2323, in the observation image FG3 displayed on the display device 4, an image loss occurs on vertical lines of the third column, the thirteenth column, . . . (the pixels of address numbers "2", "12", "22", . . . ) corresponding to the third image signal FS3 along with a loss of the third image signal FS3 as illustrated in FIG. 10C. In addition, in the observation image FG3, an image loss occurs on vertical lines of the seventh column, the seventeenth column, . . . (the pixels of address numbers "6", "16", "26", . . . ) corresponding to the seventh image signal FS7 along with a loss of the seventh image signal FS7. In addition, in the observation image FG3, an image loss occurs on vertical lines of the tenth column, the twentieth column, . . . (the pixels of address numbers "9", "19", "29", . . . ) corresponding to the tenth image signal FS10 along with a loss of the tenth image signal FS10.

The fourth distributed image signal DS4 is a combination of the fourth image signal FS4 including pieces of pixel data generated at the pixels of address numbers "3", "13", "23", . . . , and the ninth image signal FS9 including pieces of pixel data generated at the pixels of address numbers "8", "18", "28", . . . .

Thus, when a transmission failure occurs in the fourth optical fiber 2324, in the observation image FG4 displayed on the display device 4, an image loss occurs on vertical lines of the fourth column, the fourteenth column, . . . (the pixels of address numbers "3", "13", "23", . . . ) corresponding to the fourth image signal FS4 along with a loss of the fourth image signal FS4 as illustrated in FIG. 10D. In addition, in the observation image FG4, an image loss occurs on vertical lines of the ninth column, the nineteenth column, . . . (the pixels of address numbers "8", "18", "28", . . . ) corresponding to the ninth image signal FS9 along with a loss of the ninth image signal FS9.

In other words, the first to the fourth distributed image signals DS1 to DS4 are generated by combining image signals of pixels that are separate from each other with at least two pixels interposed therebetween among the first to the tenth image signals FS1 to FS10. Thus, any image loss when a transmission failure occurs in any of the first to the fourth optical fibers 2321 to 2324 occurs on vertical lines that are separate from each other with at least two pixels interposed therebetween, not on vertical lines that are adjacent to each other, as illustrated in FIGS. 10A to 10D. Any of the observation images FG1 to FG4 in which an image loss occurs on vertical lines that are separate from each other allows easier recognition thereof than an observation image in which an image loss occurs on vertical lines that are adjacent to each other.

Accordingly, the observation images FG1 to FG4 suitable for observation may be displayed when a transmission failure occurs in any of the first to the fourth optical fibers 2321 to 2324.

At least two signal transmission paths through which an identical image signal is transmitted are not included in the medical observation system 1 according to the first embodiment, thereby achieving a simplified structure without a redundant signal transmission path that is unnecessary when no transmission failure occurs.

In the medical observation system 1 according to the first embodiment, as illustrated in FIG. 9, compensation of each pixel data of the pixel group GP1 lost due to a transmission failure in any of the first to the fourth optical fibers 2321 to 2324 is performed based on pixel data of the two pixel groups GP2 and GP3 that are separate from the pixel group GP1 with one pixel interposed therebetween. In particular, as described above, the medical observation system 1 is configured such that any image loss when a transmission failure occurs in any of the first to the fourth optical fibers 2321 to 2324 occurs on vertical lines that are separate from each other with at least two pixels interposed therebetween, not on vertical lines that are adjacent to each other (FIGS. 10A to 10D). In other words, when the pixel group GP1 is lost due to a transmission failure in any of the first to the fourth optical fibers 2321 to 2324, the two pixel groups GP2 and GP3 that are separate from the pixel group GP1 with one pixel interposed therebetween are configured not to be lost due to this transmission failure.

This enables reliable compensation of each pixel data of the pixel group GP1 lost due to a transmission failure in any of the optical fibers. Thus, it is possible to compensate for any image loss on vertical lines in the observation images FG1 to FG4 (FIGS. 10A to 10D) described above, thereby forming a favorable image suitable for observation.

In the medical observation system 1 according to the first embodiment, when a transmission failure is detected, notification of predetermined information (information indicating the occurrence of the transmission failure and an optical fiber in which the transmission failure has occurred) is given through the display device 4 and the output unit 67.

This configuration allows a user such as a doctor to recognize that an observation image displayed on the display device 4 is a compensated image obtained through compensation of each pixel data of the pixel group GP1 lost due to a transmission failure in any of the first to the fourth optical fibers 2321 to 2324 with pixel data of the other pixel groups GP2 and GP3. The configuration may also suggest, to this user, replacement of the optical fiber in which the transmission failure has occurred.

Modification of First Embodiment

In the first embodiment described above, the image processing unit 63 compensates for each pixel data (component information) of a pixel group (in the example in FIG. 9, the pixel group GP1) lost due to a transmission failure in any of the first to the fourth optical fibers 2321 to 2324 based on pixel data (component information) of two pixel groups (in the example in FIG. 9, the pixel groups GP2 and GP3) that are separate from this pixel group with one pixel interposed therebetween, but the present disclosure is not limited thereto.

For example, each pixel data (component information) of a pixel group lost due to a transmission failure in any of the first to the fourth optical fibers 2321 to 2324 may be set to be pixel data of pixel groups that are adjacent to this pixel group. In the example in FIG. 9, pixel data of the pixel GP1B is set to be pixel data of pixels corresponding to the G filter groups that are adjacent to the pixel GP1B. Pixel data of the pixel GP1G is set to be pixel data of pixels corresponding to the R filter groups that are adjacent to the pixel GP1G.

For example, each pixel data (component information) of a pixel group lost due to a transmission failure in any of the first to the fourth optical fibers 2321 to 2324 may be set to be the corresponding pixel data (component information) of one pixel group that is separate from this pixel group with one pixel interposed therebetween. In the example in FIG. 9, pixel data of the pixel GP1B is set to be pixel data of the pixel GP2B or the pixel GP3B. Pixel data of the pixel GP1G is set to be pixel data of the pixel GP2G or the pixel GP3G.

Second Embodiment

The following describes a second embodiment of the present disclosure.

In the following description, any configuration identical to that in the first embodiment described above is denoted by an identical reference sign, and detailed description thereof will be omitted or simplified.

A medical observation system according to the second embodiment is different from the medical observation system 1 described in the first embodiment above in the image processing by the image processing unit 63.

Specifically, the image processing unit 63 according to the second embodiment executes, on each image signal restored by the received signal processing unit 62, different demosaic processing depending on whether a transmission failure is detected by the transmission failure detection unit 622.

Figure 11A:
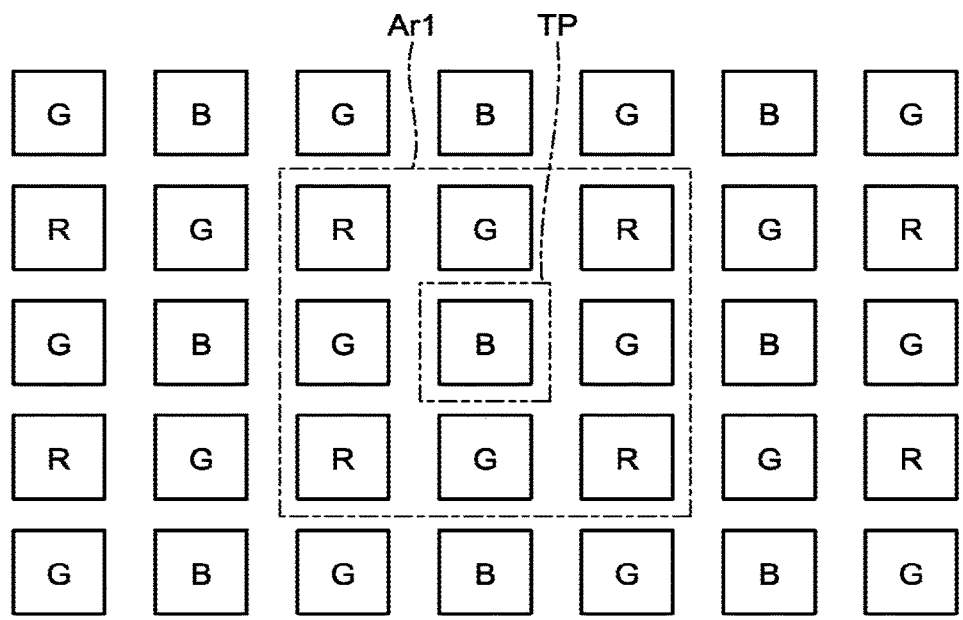
FIG. 11A is a diagram of exemplary image processing by an image processing unit according to a second embodiment of the present disclosure, illustrating demosaic processing when no transmission failure is detected by a transmission failure detection unit.
Figure 11B:
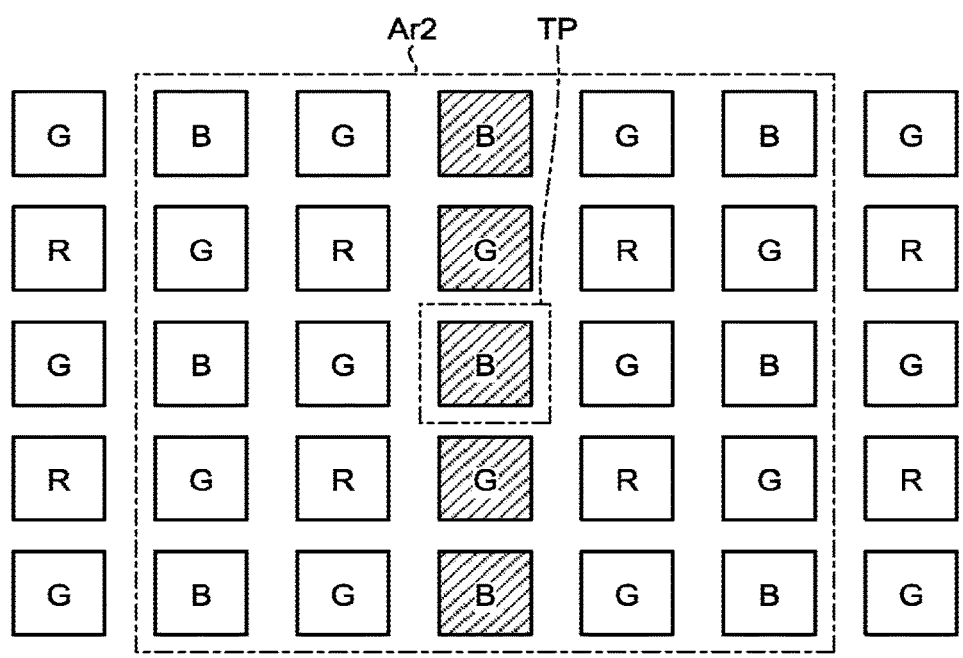
FIG. 11B is a diagram of exemplary image processing by the image processing units according to the second embodiment of the present disclosure, illustrating demosaic processing when a transmission failure is detected by the transmission failure detection unit.

FIG. 11A is a diagram of exemplary image processing by the image processing unit 63 according to the second embodiment of the present disclosure, illustrating the demosaic processing when no transmission failure is detected by the transmission failure detection unit 622. FIG. 11B is a diagram of exemplary image processing by the image processing unit 63 according to the second embodiment of the present disclosure, illustrating the demosaic processing when a transmission failure is detected by the transmission failure detection unit 622. Specifically, FIGS. 11A and 11B correspond to FIG. 9, illustrating an image in accordance with the image signal restored by the signal restoring unit 623.

In FIGS. 11A and 11B, for the purpose of illustration, similarly to FIG. 9, the character of "R" is attached to a pixel corresponding to the R filter group in the color filter 2232, the character of "G" is attached to a pixel corresponding to the G filter group, and the character of "B" is attached to a pixel corresponding to the B filter group. In FIG. 11B, similarly to FIG. 9, a pixel group lost due to a transmission failure in any of the first to the fourth optical fibers 2321 to 2324 is hatched.

Specifically, when no transmission failure is detected by the transmission failure detection unit 622, the image processing unit 63 executes, for each compensation target pixel TP (FIG. 11A), on all pixels included in the image signal restored by the signal restoring unit 623, first demosaic processing that compensates for other component information (pixel data) of the target pixel TP based on component information (pixel data) of any other pixel positioned in a first surrounding region Ar1 (FIG. 11A) centering around the target pixel TP.

For example, as illustrated in FIG. 11A, when the target pixel TP is a pixel corresponding to the B filter group, the target pixel TP includes B component information (pixel data) but not R and G component information (pixel data). Thus, the image processing unit 63 executes the first demosaic processing to compensate for R and G component information (pixel data) of the target pixel TP based on R and G component information (pixel data) of each pixel positioned in the first surrounding region Ar1 (region of 3 pixels×3 pixels) centering around the target pixel TP by one pixel. Specifically, G component information (pixel data) of the target pixel TP is set to be component information (pixel data) obtained by averaging component information (pixel data) of four pixels corresponding to the G filter group positioned above, below, left of, and right of the target pixel TP. R component information (pixel data) of the target pixel TP is set to be component information (pixel data) obtained by averaging component information (pixel data) of four pixels corresponding to the R filter group positioned obliquely above and below the target pixel TP (positioned at opposing corners of the first surrounding region Ar1). The same processing is executed also when a target pixel is a pixel corresponding to the R or the G filter group other than the B filter group.

When a transmission failure is detected by the transmission failure detection unit 622, the image processing unit 63 executes, for each compensation target pixel TP (FIG. 11B) among pixels of a pixel group lost due to this transmission failure among all pixels included in the image signal restored by the signal restoring unit 623, second demosaic processing to compensate for component information (pixel data) of the target pixel TP based on component information (pixel data) of any other pixel positioned in a second surrounding region Art (FIG. 11B) that centers around the target pixel TP and is larger than the first surrounding region Ar1. The image processing unit 63 executes the first demosaic processing described above on any pixel not in the pixel group lost due to this transmission failure among all pixels included in the image signal restored by the signal restoring unit 623.

For example, as illustrated in FIG. 11B, when the target pixel TP is a pixel corresponding to the B filter group in a pixel group lost due to a transmission failure, the target pixel TP does not include any of R, G, and B component information (pixel data) because of the lost due to the transmission failure. Thus, the image processing unit 63 executes the second demosaic processing to compensate for R, G, and B component information (pixel data) of the target pixel TP based on R, G, and B component information (pixel data) of each pixel positioned in the second surrounding region Ar2 (region of 5 pixels×5 pixels) around the target pixel TP by two pixels. Specifically, R component information (pixel data) of the target pixel TP is set to be component information (pixel data) obtained by averaging component information (pixel data) of four pixels not in the pixel group lost due to the transmission failure among pixels corresponding to the R filter group positioned in the second surrounding region Ar2. G component information (pixel data) of the target pixel TP is set to be component information (pixel data) obtained by averaging component information (pixel data) of 10 pixels not in the pixel group lost due to the transmission failure among pixels corresponding to the G filter group positioned in the second surrounding region Ar2. B component information (pixel data) of the target pixel TP is set to be component information (pixel data) obtained by averaging component information (pixel data) of six pixels not in the pixel group lost due to the transmission failure among pixels corresponding to the B filter group positioned in the second surrounding region Ar2. The same processing is executed when a target pixel is a pixel corresponding to the R or the G filter group included in a pixel group lost due to a transmission failure.

The same effect as that of the first embodiment described above is still achieved when the demosaic processing is executed as in the second embodiment described above.

Modification of Second Embodiment

In the second embodiment described above, when a transmission failure is detected by the transmission failure detection unit 622, the image processing unit 63 executes the second demosaic processing on each pixel of a pixel group lost due to this transmission failure among all pixels included in each image signal restored by the signal restoring unit 623, and executes the first demosaic processing on any pixel not in the pixel group lost due to this transmission failure, but the present disclosure is not limited thereto.

For example, when a transmission failure is detected by the transmission failure detection unit 622, the second demosaic processing may be executed on all pixels included in the image signal restored by the signal restoring unit 623.

In the second embodiment described above, the first surrounding region Ar1 is set to be the region of 3 pixels×3 pixels centering around the target pixel TP, and the second surrounding region Ar2 is set to be the region of 5 pixels×5 pixels centering around the target pixel TP, but the present disclosure is not limited thereto. When the second surrounding region Ar2 is larger than the first surrounding region Ar1, the first and the second surrounding regions Ar1 and Ar2 may be any other regions.

In the second embodiment described above, in the demosaic processing, component information (pixel data) of the target pixel TP is set to be pixel data obtained by simply averaging component information (pixel data) of other pixels, but the present disclosure is not limited to this simple averaging method. Any other method used in the well-known demosaic processing may be used.

The medical observation system 1 according to the first embodiment described above may be configured to execute the demosaic processing described in the second embodiment above.

In the first and the second embodiments described above, the electrical-optical conversion unit 225 is provided to the camera head 22, but the present disclosure is not limited thereto. For example, the electrical-optical conversion unit 225 may be provided to the first transmission cable 23 including the connector CN2. Moreover, at least part or all of the internal configuration (function) of the transmission signal processing unit 224 as the medical signal processing device according to the present disclosure may be provided to the first transmission cable 23, such as the connector CN2. In this case, an electric signal is output from the camera head 22, converted into an optical signal at the electrical-optical conversion unit 225 provided to the first transmission cable 23, and transmitted as a transmission image signal through the optical fibers 232 (signal transmission paths).

Third Embodiment

The following describes a third embodiment of the present disclosure.

In the following description, any component identical to that in the first and the second embodiments described above is denoted by an identical reference sign, and detailed description thereof will be omitted or simplified.

In the medical observation system 1 according to the first and the second embodiments described above, the present disclosure is applied to the endoscope 2 including the camera head 22.

In a medical observation system according to the third embodiment, however, the present disclosure is applied to what is called a video scope including an imaging unit at a leading end of an insertion unit of an endoscope.

Figure 12:
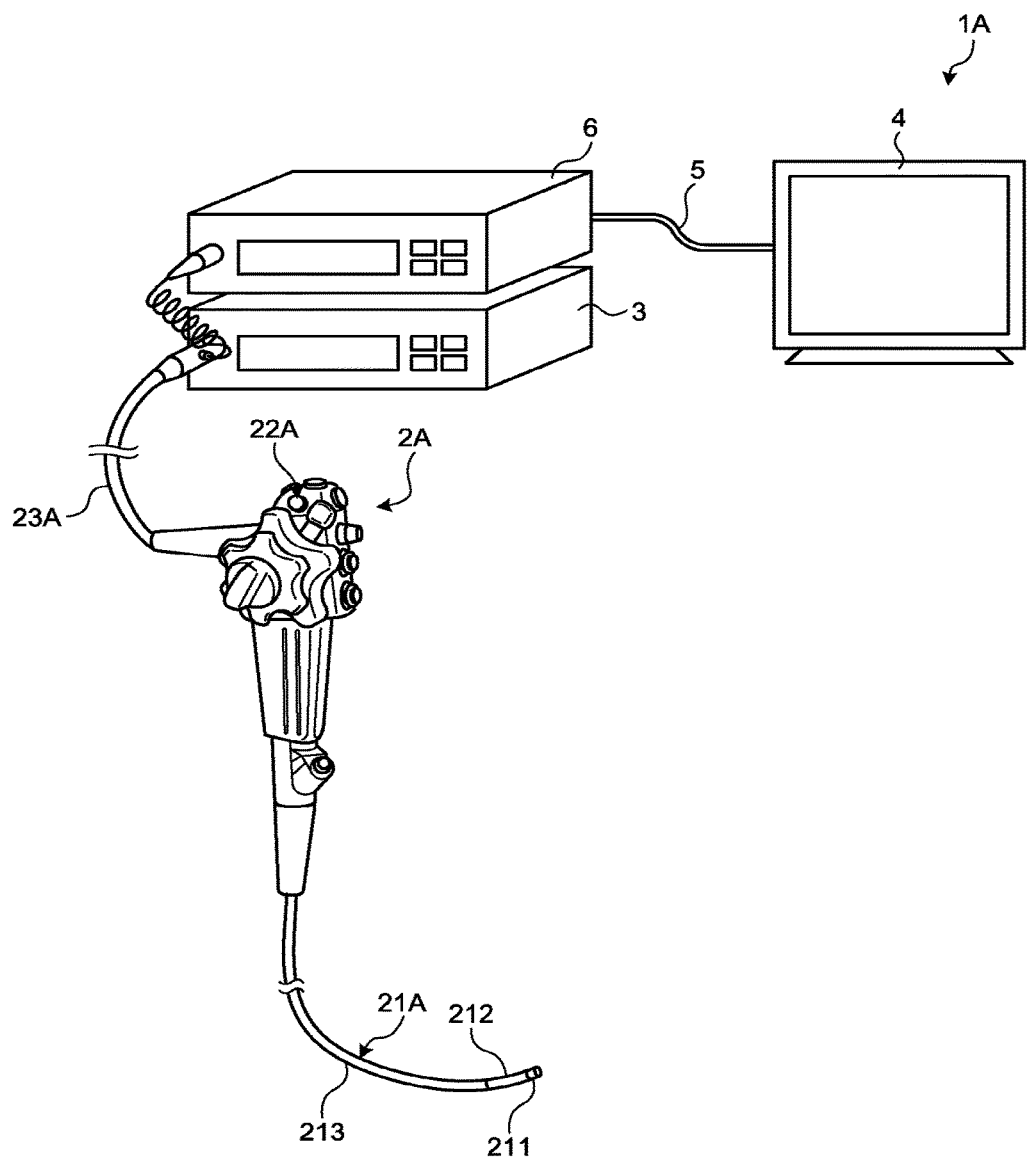
FIG. 12 is a diagram illustrating a schematic configuration of a medical observation system according to a third embodiment of the present disclosure.

FIG. 12 is a diagram illustrating a schematic configuration of a medical observation system 1A according to the third embodiment of the present disclosure.

As illustrated in FIG. 12, a medical observation system 1A according to the third embodiment includes an endoscope 2A configured to generate an image signal by capturing an image of the inside of the body at an observation site through an insertion unit 21A inserted into the inside of the living body and generate a plurality of transmission image signals from this image signal, the light source device 3 configured to generate illumination light to be emitted from a leading end of the endoscope 2A, the control device 6 (the control device described in the first or the second embodiment) configured to receive the transmission image signals generated at the endoscope 2A and process these transmission image signals, and the display device 4 connected with the control device 6 through the second transmission cable 5 and configured to display an image based on the image signals processed at the control device 6.

As illustrated in FIG. 12, the endoscope 2A includes the flexible elongated insertion unit 21A, an operation unit 22A connected with a base end side of the insertion unit 21A and configured to receive inputting of various operation signals, and a universal code 23A extending from the operation unit 22A in a direction different from a direction in which the insertion unit 21A extends and including various built-in cables connected to the light source device 3 and the control device 6.

As illustrated in FIG. 12, the insertion unit 21A includes a leading end part 211 including a built-in imaging unit (not illustrated) configured to generate an image signal by capturing an image of the inside of the living body, a bent part 212 that includes a plurality of bent pieces and may be freely bent, and an elongated flexible tube 213 connected with a base end side of the bent part 212.

Then, although not illustrated in detail, built-in components similar to the transmission signal processing unit 224 and the electrical-optical conversion unit 225 described in the first embodiment above are included inside of the operation unit 22A. The image signal generated at the imaging unit described above is processed at this transmission signal processing unit. The universal code 23A has a configuration substantially same as the first transmission cable 23 described in the first embodiment above. Then, a plurality of transmission image signals (optical signals) processed (generated) inside of the operation unit 22A (the transmission signal processing unit and the electrical-optical conversion unit) are output to the control device 6 through the universal code 23A.

When a soft endoscope (the endoscope 2A) is used as in the third embodiment described above, the same effect as that of the first embodiment described above is achieved.

Fourth Embodiment

The following describes a fourth embodiment of the present disclosure.

In the following description, any component identical to that in the first and the second embodiments described above is denoted by an identical reference sign, and detailed description thereof will be omitted or simplified.

In the medical observation system 1 according to the first and the second embodiments described above, the present disclosure is applied to the endoscope 2 including the camera head 22.

In a medical observation system according to the fourth embodiment, however, the present disclosure is applied to a surgical microscope configured to capture an enlarged image of a predetermined viewing region in the inside of a subject (the inside of a living body) or on the surface of the subject (the surface of the living body).

Figure 13:
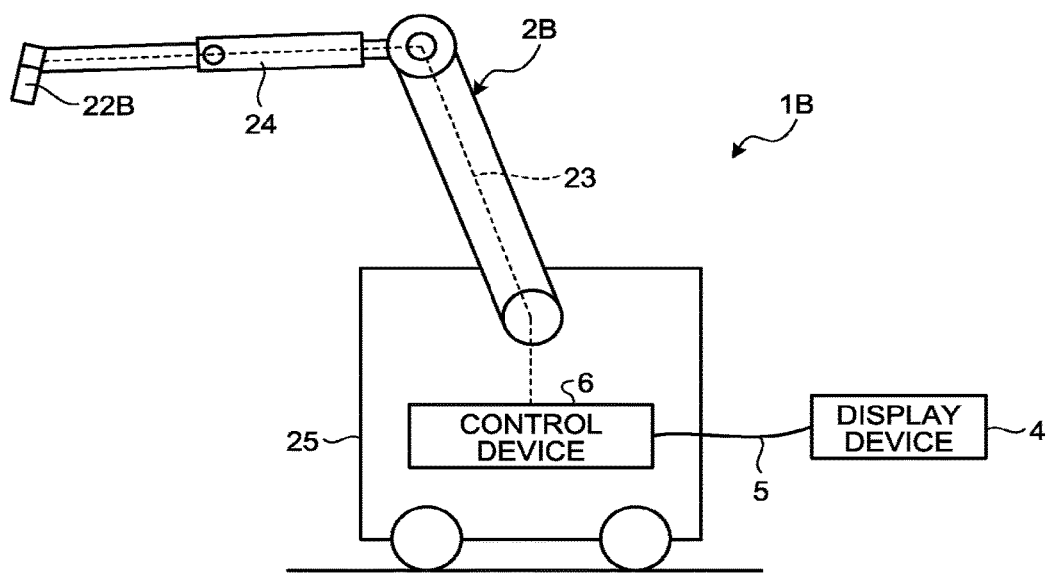
FIG. 13 is a diagram illustrating a schematic configuration of a medical observation system according to a fourth embodiment of the present disclosure.

FIG. 13 is a diagram illustrating a schematic configuration of a medical observation system 1B according to the fourth embodiment of the present disclosure.

As illustrated in FIG. 12, a medical observation system 1B according to the fourth embodiment includes a surgical microscope 2B configured to generate an image signal by capturing an image for observing an object and generate a plurality of transmission image signals from this image signal, the control device 6 (the control device described in the first or the second embodiment) configured to receive the transmission image signals generated at the surgical microscope 2B and process these transmission image signals, and the display device 4 connected with the control device 6 through the second transmission cable 5 and configured to display an image based on the image signals processed at the control device 6.

As illustrated in FIG. 13, the surgical microscope 2B includes a microscope unit 22B configured to generate an image signal by capturing an enlarged image of a small site of the object and generate a plurality of transmission image signals from this image signal, a support unit 24 connected with a base end part of the microscope unit 22B and including an arm rotatably supporting the microscope unit 22B, and a base unit 25 rotatably holding a base end part of the support unit 24 and movable on a floor surface.

As illustrated in FIG. 13, the control device 6 is installed in the base unit 25.

Instead of being provide movable on the floor surface, the base unit 25 may be fixed on, for example, a ceiling or a wall surface to support the support unit 24. The base unit 25 may include a light source unit configured to generate illumination light to be emitted to the object from the surgical microscope 2B.

Although not illustrated in detail specific, the microscope unit 22B includes an imaging unit configured to generate an image signal by capturing an image of the inside of the living body, and built-in components similar to the transmission signal processing unit 224 and the electrical-optical conversion unit 225 described in the first embodiment above. The image signal generated at the imaging unit is processed at the transmission signal processing unit. Then, a plurality of transmission image signals (optical signals) processed (generated) at the microscope unit 22B (the transmission signal processing unit and the electrical-optical conversion unit) are output to the control device 6 through the first transmission cable 23 wired along the support unit 24.

When the surgical microscope 2B is used as in the fourth embodiment described above, the same effect as that of the first embodiment described above is achieved.

Other Embodiments

The configurations to achieve the present disclosure are described above, but the present disclosure is not limited to the first to the fourth embodiments described above.

In the first to the fourth embodiments described above, a plurality of transmission image signals are transmitted as optical signals from the camera head 22, the operation unit 22A, and the microscope unit 22B to the control device 6, but the present disclosure is not limited thereto. The transmission image signals may be transmitted as electric signals. In other words, the optical fibers 232 as signal transmission paths according to the present disclosure included in the first transmission cable 23 and the universal code 23A may be replaced with electric wires. In this case, the electrical-optical conversion unit 225 and the optical-electrical conversion unit 61 are omitted.

In the transmission signal processing unit 224 according to the first to the fourth embodiments described above, the auxiliary data addition processing is executed after the mapping processing, but the present disclosure is not limited thereto. The mapping processing may be executed after the auxiliary data addition processing (in which auxiliary data is added to the first to the tenth image signals FS1 to FS10, and the first to the fourth transmission image signals TS1 to TS4 are generated by distributing the first to the tenth image signals FS1 to FS10 to which this auxiliary data is added).

In the first to the fourth embodiments described above, the scheme of combination of the first to the tenth image signals FS1 to FS10 when the first to the fourth distributed image signals DS1 to DS4 are generated is not limited to the combination schemes described in the first to the fourth embodiments described above. Any other combination scheme may be employed in which image signals of pixels that are separate from each other with at least one pixel interposed therebetween are combined.

In the first to the fourth embodiments described above, the image processing illustrated in FIGS. 9 and 11B compensates for each pixel data of a pixel group lost due to a transmission failure in any of the first to the fourth optical fibers 2321 to 2324, but the present disclosure is not limited thereto.

For example, such image processing may be used that compensates for each pixel data of this lost pixel group to achieve substantially same luminance values between a pixel group lost due to a transmission failure in any of the first to the fourth optical fibers 2321 to 2324 and pixel groups that are adjacent to this lost pixel group.

A medical signal processing device according to the present disclosure generates a plurality of distributed image signals by combining, among a plurality of pixel data groups input in the medical signal processing device in parallel, pixel data groups of respective pixels that are separate from each other. The distributed image signals are transmitted to an external medical control device through a plurality of respective signal transmission paths.

A transmission failure that has occurred in any of the signal transmission paths results in a loss of a distributed image signal corresponding to a signal transmission path in which this transmission failure has occurred. However, this distributed image signal is a combination of pixel data groups of respective pixels that are separate from each other. Thus, any loss of a distributed image signal when a transmission failure occurs in any of the signal transmission paths occurs at pixels that are separate from each other, not at pixels that are adjacent to each other. An image in which a loss of a distributed image signal occurs at pixels that are separate from each other allows easier recognition thereof than an image in which a loss of a distributed image signal occurs at pixels that are adjacent to each other.

With this configuration, an image suitable for observation may be continuously displayed when a transmission failure occurs in a signal transmission path. In addition, a simplified structure without a redundant signal transmission path that is unnecessary when no transmission failure occurs may be achieved because the distributed image signals different from each other are transmitted to the external medical control device through the respective signal transmission paths.

A medical observation system according to the present disclosure includes the medical signal processing device and the medical control device described above, and thus provides an effect similar to the above-described effect of the medical signal processing device.

It should be understood by those skilled in the art that various modifications, combinations, sub-combinations and alterations may occur depending on design requirements and other factors insofar as they are within the scope of the appended claims or the equivalents thereof.

Disclosure

What is claimed is:

1. A medical signal processing device comprising:
    circuitry comprising hardware and configured to receive an image signal including a plurality of pixel data groups in parallel, generate a plurality of distributed image signals by combining, among the plurality of pixel data groups, pixel data groups of respective pixels that are separate from each other, and transmit the plurality of distributed image signals to an external medical control device through a plurality of respective signal transmission paths,
    wherein the plurality of pixel data group are groups of respective pixels arrayed at a constant interval among pixels sequentially arrayed in a predetermined direction in an image made of pixels arrayed in a matrix, and
    wherein the plurality of pixel data groups are data of respective pixels that are different from each other.

2. The medical signal processing device according to claim 1, wherein the circuitry is configured to combine, among the plurality of pixel data groups, pixel data groups of respective pixels that are separate from each other with at least two pixels interposed therebetween.

3. A medical observation system comprising:
    first circuitry comprising hardware and configured to receive an image signal including a plurality of pixel data groups in parallel and generate a plurality of distributed image signals by combining, among the plurality of pixel data groups, pixel data groups of respective pixels that are separate from each other,
    wherein the plurality of pixel data groups are groups of respective pixels arrayed at a constant interval among pixels sequentially arrayed in a predetermined direction in an image made of pixels arrayed in a matrix, and
    wherein the plurality of pixel data groups are data of respective pixels that are different from each other;
    a plurality of signal transmission paths through which the distributed image signals from the first circuitry are respectively transmitted; and
    a medical control device including second circuitry comprising hardware and configured to receive the distributed image signals through the signal transmission paths and restore the image signal based on the distributed image signals.

4. The medical observation system according to claim 3, wherein the second circuitry is configured to:
    detect a signal transmission failure in the signal transmission paths; and
    provide the image signal restored by the medical control device with image processing in accordance with a result of the detection of the signal transmission failure.

5. The medical observation system according to claim 4, further comprising:
    an imaging unit including a color filter in which filters sorted in three filter groups corresponding to R, G, and B wavelength bands are arrayed in a predetermined format, and
    an image sensor having a light-receiving surface on which the color filter is provided, wherein
    the imaging unit is configured to generate the image signal including component information of any of R, G, and B for each of a plurality of the pixels in response to incident light through the color filter, and output the image signal to the first circuitry, and
    when a transmission failure is detected, the second circuitry is configured to compensate for component information of a pixel lost due to the transmission failure based on component information of two other pixels that are adjacent to the lost pixel among pixels corresponding to the filter group of the lost pixel.

6. The medical observation system according to claim 4, further comprising:
    an imaging unit including a color filter in which filters sorted in three filter groups corresponding to R, G, and B wavelength bands are arrayed in a predetermined format, and
    an image sensor having a light-receiving surface on which the color filter is provided, wherein
    the imaging unit is configured to generate the image signal including any of R, G, and B component information for each of a plurality of the pixels in response to incident light through the color filter, and output the image signal to the first circuitry,
    when no transmission failure is detected, the second circuitry is configured to execute, for each compensation target pixel, on all of the pixels included in the image signal, first demosaic processing that compensates for other component information of the target pixel based on component information of other pixels positioned in a first surrounding region that centers around the target pixel in the image, and
    when a transmission failure is detected, the second circuitry is configured to compensate execute, for each compensation target pixel, at least on a pixel lost due to the transmission failure among the pixels included in the image signal, second demosaic processing that compensates for component information of the target pixel based on component information of other pixels positioned in a second surrounding region that centers around the target pixel in the image and is larger than the first surrounding region.

7. The medical observation system according to claim 3, wherein the second circuitry is configured to:

detect a signal transmission failure in the signal transmission paths; and give notification of predetermined information when a transmission failure is detected.

8. The medical observation system according to claim 3, wherein the signal transmission paths each include a light transmission path through which an optical signal is transmitted, and the medical observation system further comprises:

an electrical-optical conversion unit configured to convert a plurality of electric signals based on the distributed image signals into a plurality of respective optical signals and output the optical signals to the signal transmission paths, and an optical-electrical conversion unit configured to convert the optical signals received through the signal transmission paths into a plurality of respective electric signals and output the electric signals to the medical control device.

* * * * *